United States Patent [19]

Maschler et al.

[11] Patent Number: 5,268,296
[45] Date of Patent: Dec. 7, 1993

[54] DNA VECTOR AND RECOMBINANT HOST CELL FOR PRODUCTION OF HIRULLIN P6 AND P18

[75] Inventors: Reinhard Maschler, Oldenburg, Fed. Rep. of Germany; Verena Steiner, Basel, Switzerland; Markus G. Grütter, Hochwald, Switzerland

[73] Assignees: Ciba-Geigy Corporation, Ardsley, N.Y.; UCP Gen-Pharma, AG, Kirchberg, Switzerland

[21] Appl. No.: 839,644

[22] Filed: Feb. 21, 1992

Related U.S. Application Data

[62] Division of Ser. No. 363,648, Jun. 8, 1989, Pat. No. 5,114,922.

[30] Foreign Application Priority Data

Jun. 11, 1988 [GB] United Kingdom ................ 8813876
Jul. 29, 1988 [GB] United Kingdom ................ 8818123

[51] Int. Cl.$^5$ ...................... C12N 1/21; C12N 15/15; C12N 15/09; C12N 15/74
[52] U.S. Cl. .............................. 435/252.3; 435/69.1; 435/172.3; 435/320.1; 435/942; 536/23.5
[58] Field of Search ............... 435/69.1, 172.3, 252.3, 435/320.1, 942; 530/333, 344, 324; 536/27, 23.5

[56] References Cited

U.S. PATENT DOCUMENTS

| | | | |
|---|---|---|---|
| 4,636,489 | 1/1987 | Seemuller et al. | 514/12 |
| 4,654,302 | 3/1987 | Fritz et al. | 435/70 |
| 4,668,662 | 5/1987 | Tripier | 514/12 |
| 4,767,742 | 8/1988 | Dodt et al. | 514/12 |
| 4,791,100 | 12/1988 | Kramer et al. | 514/12 |
| 5,087,613 | 2/1992 | Courtney et al. | 435/69.6 |
| 5,095,092 | 3/1992 | Badziong et al. | 530/324 |

FOREIGN PATENT DOCUMENTS 0225633 6/1987 European Pat. Off. .
0263608 4/1988 European Pat. Off. .
0373767 6/1990 European Pat. Off. .

OTHER PUBLICATIONS

R. T. Sawyer, *Leech Biology and Behaviour* (3 volumes), Oxford Science Publications, pp. 490–505 (1986).
Rigbi et al., *Comp. Biochem. Physiol.*, 87B:567–573 (1987).
Goldstein et al., Chemical Abstract No. 105:38092f (1986).
Seemuller et al., Proteinase Inhibitors, Barrett and Salveson (eds.), pp. 337–344 (1986).

*Primary Examiner*—Robert A. Wax
*Assistant Examiner*—Stephen Walsh
*Attorney, Agent, or Firm*—Shawn P. Foley

[57] ABSTRACT

Novel polypeptides, designated hirullins, have a strong antithrombic activity and can therefore be used for the therapy and prophylaxis of thromboses. Said compounds are isolated from the leech *Hirudinaria manillensis* or are produced by conventional peptide synthesis or by recombinant DNA techniques. DNA sequences encoding hirullins P6 and P18 are supplied, hybrid vectors and transformed microorganisms for recombinant hirullin production are supplied.

3 Claims, 6 Drawing Sheets

```
       EcoRI                          PHO5 SS
                    MetPheLysSerValValTyrSerIleLeuAlaAlaSerLeuAlaAsnAla
       <------------------1------------------><-------------------3----
       AATTCAAAATGTTTAAATCTGTTGTTTATTCAATTTTAGCCGCTTCTTTGGCCAATGCA
           GTTTTACAAATTTAGACAACAAATAAGTTAAAATCGGCGAAGAAACCGGTTACGT
           <--------------------------2----------------------><-

----> P6
       MetArgTyrThrAlaCysThrGluSerGlyGlnAsnGlnCysIleCysGluGlyAsn
       ---------------><--------------------------5----------
       ATGAGATACACTGCTTGTACTGAATCTGGTCAAAACCAATGTATTTGTGAAGGTAAC
       TACTCTATGTGACGAACATGACTTAGACCAGTTTTGGTTACATAAACACTTCCATTG
       -------------------4-------------------><------------

AspValCysGlyGlnGlyArgAsnCysGlnPheAspSerSerGlyLysLysCysValGlu
       ----------><-----------------7------
       GACGTTTGTGGTCAAGGTAGAAACTGTCAATTCGACTCTTCTGGTAAGAAGTGTGTTGAA
       CTGCAAACACCAGTTCCATCTTTGACAGTTAAGCTGAGAAGACCATTCTTCACACAACTT
       -------------6-------------------><-----------------------8---

GlyGluGlyThrArgLysProGlnAsnGluGlyGlnHisAspPheAspProIleProGlu
       ><-----------------9------------><-----------------11-------
       GGTGAAGGTACTAGAAAGCCACAAAACGAAGGTCAACACGACTTCGACCCAATTCCAGAA
       CCACTTCCATGATCTTTCGGTGTTTTGCTTCCAGTTGTGCTGAAGCTGGGTTAAGGTCTT
       --------------------><-------------10------------><---------

GluTyrLeuSer
       -------------------->
       GAATACTTGTCTTAG
       CTTATGAACAGAATCCTAG
       -----12------------>
                        BamHI
```

FIG. 1

```
        EcoRI                          PHO5 SS
                    MetPheLysSerValValTyrSerIleLeuAlaAlaSerLeuAlaAsnAla
        <----------------------1--------------------><-------------3--
        AATTCAAAATGTTTAAATCTGTTGTTTATTCAATTTTAGCCGCTTCTTTGGCCAATGCA
            GTTTTACAAATTTAGACAACAAATAAGTTAAAATCGGCGAAGAAACCGGTTACGT
            <----------------------------2----------------><----------

---->  P18
              ValSerTyrThrAspCysThrSerGlyGlnAsnTyrCysLeuCysGlyGlyAsnPhe
        ---------------------------><-----------------5---------------
        GTTTCTTACACTGACTGTACTTCTGGTCAAAACTACTGTTTGTGTGGTGGTAACTTC
        CAAAGAATGTGACTGACATGAAGACCAGTTTTGATGACAAACACACCACCATTGAAG
        --------------------------4-----------------><------------

CysGlyAspGlyLysHisCysGluMetAspGlySerGluAsnLysCysValAspGlyGlu
        ----><---------------------------7--------------------><------
        TGTGGTGACGGTAAGCACTGTGAAATGGACGGTTCTGAAAACAAGTGTGTTGACGGTGAA
        ACACCACTGCCATTCGTGACACTTTACCTGCCAAGACTTTTGTTCACACAACTGCCACTT
        ------------6------------------><-----------------------8-----

GlyThrProLysArgGlnThrSerGlyProSerAspPheGluGluPheSerLeuAspAsp
        ----------------9--------------><------------------11---------
        GGTACTCCAAAGAGACAAACTTCTGGTCCATCTGACTTCGAAGAATTTTCTTTGGACGAC
        CCATGAGGTTTCTCTGTTTGAAGACCAGGTAGACTGAAGCTTCTTAAAAGAAACCTGCTG
        -------><------------------10--------------------------><---

IleGluGln
        ----------->
        ATTGAACAATAG
        TAACTTGTTATCCTAG
        -------12--------->
                        BamHI
```

FIG. 2

DNA VECTOR AND RECOMBINANT HOST CELL FOR PRODUCTION OF HIRULLIN P6 AND P18

CROSS-REFERENCE TO RELATED APPLICATION

This is a divisional of Ser. No. 363,648, filed Jun. 8, 1989, now U.S. Pat. No. 5,114,922, issued May 19, 1992.

The present invention relates to novel polypeptides having an anti-coagulant activity, to methods and means for the preparation thereof, to pharmaceutical compositions containing such polypeptides and to their use as anticoagulant agents.

Medicinal leeches (*Hirudo medicinalis*) have been used for centuries in therapy. Among the many biologically active peptides occurring in leech saliva hirudin is of special interest as it is the strongest thrombin inhibitor known. Hirudin reacts specifically with thrombin and thus prevents blood coagulation. It is non-antigenic, has a low toxicity and the unaltered molecule is almost completely excreted via the kidneys. Isolation, purification and the pharmaceutical properties of hirudin have been reviewed by P. Walsmann et al. [Pharmazie 36, 653 (1981)] and its primary structure has been elucidated by J. Dodt et al. [Biol. Chem. Hoppe-Seyler 366, 379 (1985)].

Recently, cDNAs and synthetic genes coding for hirudin or hirudin variants have been cloned and expressed in microbial hosts such as *Escherichia coli* and *Saccharomyces cerevisiae* [cf. European Patent Applications No. 158 564 and 168 342). Although the expression products lack the sulphate monoester group at Tyr$^{63}$- —and were therefore designated "desulphatohirudins"— they turned out to exhibit approximately the same biological activity as the natural hirudin in which the tyrosin residue is present as sulphate monoester.

Although the high therapeutic potential of hirudin is incontestable and generally acknowledged the comparably short half-life of hirudin when administered to animals [cf. F. Markwardt, Biomed. Biochem. Acta 46, 237 (1987)] is a potential problem which remains to be solved by further investigations. Considering this drawback and the utmost usefulness of antithrombotic agents for the prophylaxis and therapy of thromboses and similar conditions there is a strong need for polypeptides which are comparable to hirudin with respect to antithrombotic activity and, advantageously, exhibit a longer duration of action. It is an object of the present invention to provide such antithrombotically active polypeptides.

Surprisingly, it has been found that the leech *Hirudinaria manillensis* produces polypeptides, designated hirullins, which show a remote relationship to hirudin in structural respects and exhibit strong antithrombotic activities.

Accordingly, the invention relates to a polypeptide selected from the group consisting of the polypeptide of 63 amino acids which has the amino acid sequence

MRYTACTESG QNQCICEGND VCGQGRNCQF DSSGKKCVEG EGT*RKPQNEG QHDFDPIPEE YLS (I)

and the polypeptide of 62 amino acids which has the amino acid sequence

VSYTDCTSGQ NYCLCGGNFC GDGKHCEMDG SENKCVDGEG TPKRQT*SGPS DFEEFSLDDI EQ (II)

wherein T* represents threonine the hydroxy group of which is free or glycosylated and Z represents the phenolic hydrogen atom of tyrosine or a group —SO$_3$H, and salts thereof.

The polypeptides of the formula I are designated "desulphatohirullin P6" (Z is hydrogen) or "hirullin P6" (Z is the group —SO$_3$H). The polypeptide of the formula II is designated "hirullin P18".

The single letter code used in formulae I and II designates the following amino acids: (A) alanine, (C) cysteine, (D) aspartic acid, (E) glutamic acid, (F) phenylalanine, (G) glycine, (H) histidine, (I) isoleucine, (K) lysine, (L) leucine, (M) methionine, (N) asparagine, (P) proline, (Q) glutamine, (R) arginine, (S) serine, (T) threonine, (V) valine, (Y) tyrosine.

The glycosyl radical O-linked to threonine T* in the compound of the formula II produced by the leech *H. manillensis* can be represented by the formula —SNAc—S—Fuc          (A)

in which SNAc is either N-acetylgalactosamine or N-acetylglucosamine, S is either galactose or mannose or glucose and Fuc is fucose. The compounds of the formula I produced by the leech *H. manillensis* have for the most part a glycosyl radical O-linked to threonine T* which can be represented by the formula —SNAc—S          (B)

in which SNAc and S have the meanings given above. A minor part of compounds of the formula I produced by the leech *H. manillensis* include a threonine radical T* which carries a glycosyl radical of the formula (A) shown above.

The compounds of the invention can be in the free form or in the form of their salts. As they contain free amino and guanidino groups in several amino acid residues, the compounds of the invention can be in the form of acid addition salts. Suitable acid addition salts are in particular physiologically tolerable salts with conventional therapeutically acceptable acids. Representative inorganic acids are hydrohalic acids (such as hydrochloric acid), and also sulfuric acid, phosphoric acid and pyrophosphoric acid. Representative organic acids are in particular arenesulfonic acids (such as benzenesulfonic or p-toluenesulfonic acid), or lower alkanesulfonic acids (such as methanesulfonic acid), as well as carboxylic acids such as acetic acid, lactic acid, palmitic acid, stearic acid, malic acid, tartaric acid, ascorbic acid and citric acid. As, however, the hirullins also contain free carboxyl groups in several amino acid residues, which carboxyl groups impart acidic character to the entire peptide, they can also be in the form of salts, e.g. sodium, potassium, calcium or magnesium salts, or also as ammonium salts derived from ammonia or a physiologically tolerable organic nitrogen-containing base. However, as they contain at the same time free carboxyl groups and free amino (guanidino) groups, they can also be in the form of inner salts.

One method for the production of the new polypeptides comprises isolating said polypeptides from the bodies of the leech species *Hirudinaria manillensis* by a combination of precipation methods and chromatographic methods and, if desired, removing in a compound of the formula I obtained wherein Z is the group —SO₃H the sulfuric acid monoester group by hydrolysis, and/or, if desired, removing the glycosyl residue in a compound of the formula I or II obtained by hydrolysis or acidolysis, and/or, if desired, converting an obtained polypeptide having free carboxy and/or amino groups into a salt or converting a salt obtained into the free compound.

Isolation of hirullins from *Hirudinaria manillensis*

The isolation of the hirullins according to the invention is done in a manner known per se. Thus, leeches belonging to the species *Hirudinaria manillensis* (occurring, for example, in China) are gathered, killed and are subsequently frozen. Preferably, whole leeches are processed although the head parts which contain more hirullin may also be used. However, decapitation is a very time-consuming process since thousands of leeches are required to obtain a minimum quantity of pure material. Before extraction, the frozen leeches are ground in a blade homogenizer. Crude hirullins precipitate in cold organic solvents such as acetone or ethanol. A suitable method which can be adapted has been described by D. Bagdy et al. [Thromb. Res. 2, 229 (1973)]. The precipitate is preferably dried by lyophilisation and kept cold and dry before further purification.

The crude extract obtained is subjected to a combination of chromatographic methods such as, for example, gel filtration, affinity chromatography using polyclonal or, preferably, monoclonal antihirullin antibodies (which can be made by methods known in the art), or, in particular, thrombin as affinity reagent, reversed phase high performance liquid chromatography, ion exchange chromatography such as cation or anion exchange chromatography, chromatography on silica gel, alumina or hydroxyapatit, and the like.

As a first purification step, gel filtration is very useful because higher molecular weight proteins (such as digestive enzymes ) are separated from the 7000 dalton hirullins. The gel filtration is a method known per se. Appropriate gels are based on dextrans, dextran-acrylamides, polyacrylamides and the like. A specific gel filtration procedure has been described by J. Dodt [Biol. Chem. Hoppe-Seyler 367, 803 (1986)] and makes use of Sephadex G 75 (a dextran cross-linked with epichlorhydrin) and a buffer pH 7.8 containing 0.3M NaCl. However, Sephadex G 50 superfine is preferred because of better resolution. As an eluent, 0.1M acetic acid is very convenient because a following desalting step can be omitted. Other volatile eluents such as formic acid, pyridine-acetic acid or trimethylamine-formic acid can also be used. The sample is dissolved in the eluent at a protein concentration of 30–70 mg/ml, preferably 50 mg/ml in a volume amounting to 5% of the bed volume at the most and applied onto the preequilibrated column.

In a second purification step the eluate of the gel filtration may be subjected to affinity chromatography with thrombin bound to an appropriate matrix, such as Affigel or cyanogen bromide activated Sepharose. The thrombin column can be prepared in the following way: As a first step, commercially available thrombin is purified by gel filtration. As eluent a buffer in the pH range of 6 to 7.5 is used. The activity of the fractions can be detected with a blood coagulation test [F. Markwardt et al. Thromb. Haemost. 47, 226 (1987)]. In a next step, the active fractions are pooled and coupled to an affinity support, e.g. Affigels (Biorad) as described by the manufacturer. The elution of thrombin inhibitors is carried out with benzamidine. This latter process is described by P. Walsmann [Pharmazie 36, 860 (1981)]. Accordingly, the sample containing the active hirullins is dissolved in diluted NaCl solution at a concentration of 10 to 50 mg protein/ml. Per ml bed volume about 30 mg protein are applied. The non bound proteins are washed away with saline or diluted sodium acetate solution before the bound peptides are eluted with benzamidine. The affinity column can be combined with a gel filtration column in order to separate benzamidine from the hirullins. Active fractions are desalted and dried by lyophilization.

An alternative to affinity chromatography as described above is purification by anion exchange chromatography. Since the isoelectric point of hirullins is in the range of pH 4, application of sample at a pH between 5 to 5.6 is preferred because thus a considerable amount of unwanted proteins can be washed away with saline before elution of the active fractions. Since hirullins elute at high salt concentrations, the whole hirullin family can be eluted with a step gradient. The coeluted contaminants can easily be separated in the subsequent purification step. If instead of a step gradient a shallow salt gradient is applied, it is possible to separate isoforms of hirullins.

During the final purification isoforms of hirullins are separated from each other. Final purification includes preferably at least two different steps. For example, the peptide family is applied onto a RP C18 HPLC column and gradient eluted with water/acetonitril containing 0.1%, trifluoroacetic acid (TFA). Single peak fractions are collected and rechromatographed under the same conditions. Then, the single peak fractions are subjected to another ion pair reagent, such as heptafluorobutyric acid instead of TFA, or another stationary phase, e.g. RP silica phenyl packing. Instead of reversed phase separation, high resolution ion-exchange chromatography, e.g. with MonoQ columns on the Pharmacia FPLC system, is preferred as a last step in purification. When volatile eluents, e.g. formic acid/ammonia, are used a desalting step can be omitted.

In a compound of the formula I obtained wherein Z is the group —SO₃H the group —SO₃H can be removed by hydrolysis. Hydrolysis is preferably performed by using specific enzymes, namely arylsulfatases, which cleave the phenolic sulfate ester groups to free phenolic hydroxy groups under mild conditions. The biological cleavage of the sulfated hydroxyl group can be effected with the aid of a suitable enzyme preparation with enriched active component or of an isolated enzyme; or else a suitable enzyme system can be employed in situ, i.e. one that is directly present in a living or dead biological material, for example a growing or quiescent microorganism, a cell culture, a cell homogenate or an autolysate. In particular, the compounds of the invention are treated in an aqueous, preferably buffered, solution or suspension with an individual arylsulfatase preparation, e.g. the arylsulfatase of *Helix pomatia*, at a temperature normally employed for enzymatic processes, for example in the range from about 20° to 45° C. and preferably from 25° to 30° C. A weakly acid reaction is preferred, i.e. at a pH of about 4 to 7, in particular from about 5 to 6, which value is adjusted with a buffer such as an approximately 0.03 to 0.3 molar solution of a salt of an organic carboxylic acid with an alkali metal or with an organic base, e.g. with sodium acetate or, preferably, pyridine acetate (of about pH 5.4). The ratio of enzyme employed to the substrate (hirullin) depends in general on the activity of the respective preparation and is usually from about 1:1 to 1:100, preferably from about 1:5 to 1:20. It is advantageous to use enzymes of the greatest possible purity and activity. As the arylsulfatase catalyses not only the removal but also the introduction of the sulfate group and effects the adjustment of an equilibrium between starting materials and final products, it is advantageous to determine by preliminary experiments, for each enzyme preparation, the optimum concentration, the ratio to the substrate, and the time required for the desulfation. As a rule, the reaction is complete after a few minutes. However, the quality of the reaction product is not impaired even on longer contact (up to about 4 hours) with the active enzyme (e.g. when the reaction mixture is allowed to stand).

The course of the enzymic desulfation can be followed by bioanalysis of samples taken from the reaction mixture. For example, the enzyme activity is destroyed by heating the sample briefly (for about 3 minutes) to about 100° C., and the substrate is treated with carboxypeptidase Y. As a rule, the degradation of the peptide chain is so far advanced after about 15 minutes that the sulfated and/or free amino acid in position 61 ($Tyr^{61}$) is completely split off and is thus made available for determination in a conventional amino acid analyser.

In a compound of the formula I or II obtained containing an O-linked glycosyl radical the glycosyl radical can be removed in a manner known per se, for example by hydrolysis or acidolysis, such as by treatment with trifluorometbanesulfonic acid in an inert solvent, for example anisole, preferably with cooling in order to keep the reaction temperature at about 0° to 5° C. Other procedures known from the literature can be used as well.

An alternative method for the production of the new polypeptides comprises chemically synthesizing said polypeptides by peptide synthesis. The synthesis can be performed in a manner known per se (see, for example, Houben-Weyl, volumes 15/1 and 15/2; Synthese von Peptiden (ed. E. Wunsch); Georg Thieme Verlag Stuttgart 1974] using suitably protected amino acids. For example, short peptide fragments comprising for example up to 12 amino acid residues can be prepared and thereupon condensed in the predetermined order to yield the polypeptides according to the invention. Another approach consists in the stepwise elongation of the peptide chain on a polymeric support (Merrifield synthesis). For the synthesis of polypeptides including an O-glycosylated threonine radical and/or on O-sulphated tyrosine radical corresponding threonine and/or tyrosine units are used which already contain such O-substituents, and the reaction conditions are chosen such that the glycosyl threonyl and/or sulphato tyrosyl units remain intact.

A third especially preferred method for the production of the polypeptides according to the invention, especially those which do not contain any glycosylated threonine and/or sulfated tyrosine radicals, makes use in a manner known per se of recombinant DNA techniques. The method comprises culturing host cells transformed with a hybrid vector comprising a promoter operably linked to a DNA sequence coding for any of said polypeptides, and isolating said polypeptides and, if desired, converting an obtained polypeptide having free carboxy and/or amino groups into a salt or converting a salt obtained into the free polypeptide. More especially, the method is characterized by the steps comprising a. providing a DNA that codes for a hirullin polypeptide according to the invention,
b. inserting this DNA into a vector,
c. introducing the resulting hybrid vector into a host organism by transformation,
d. culturing the transformed host organism under conditions that permit expression of the hirullin polypeptide, and
e. isolating the hirullin polypeptide or a salt thereof.

DNAs coding for hirullins

The invention relates to a DNA that codes for a hirullin polypeptide, especially for hirullin P6 or hirullin P18.

The DNAs of the invention preferably have at their ends short flanking sequences comprising for example 3 to 10 nucleotides that include suitable restriction sites and that render possible the insertion of the DNA into a vector.

The DNAs of the invention can be produced according to processes that are known per se. For example, the DNAs can be produced chemically, or fragments thereof can be produced by chemical synthesis and linked enzymatically in a predetermined manner.

The chemical synthesis of DNAs is carried out by processes that are known per se. Suitable procedures are described by S. A. Narang [Tetrahedron 39, 3 (1983)] and in European Patent Application No. 146785.

Production of hybrid vectors that contain a DNA coding for a hirullin polypeptide The invention relates furthermore to a hybrid vector that contains a DNA sequence coding for a hirullin polypeptide, which DNA sequence is controlled in such a manner by an expression control sequence that the hirullin polypeptide is expressed in a host cell transformed with this expression vector.

The hybrid vectors of the present invention are produced, for example, by so inserting a DNA sequence coding for the hirullin polypeptide into a vector DNA that contains an expression control sequence that the expression control sequence controls the said DNA sequence.

The choice of a suitable vector is based on the host cell provided for the transformation. Suitable hosts are, for example, microorganisms, such as yeasts, for example *Saccharomyces cerevisiae,* and strains of bacteria, especially strains of *Escherichia coli,* and also *Bacillus subtilis,* as well as cells of higher organisms, especially established human or animal cell lines. Preferred host cells are strains of *S. cerevisiae.*

In principle any vector is suitable that replicates and expresses in the selected host the DNA sequences of the invention coding for the hirullin polypeptides.

Examples of vectors that are suitable for the expression of the hirullin polypeptides in an *E. coli* strain are bacteriophages, for example derivatives of bacteriophage, or plasmids, such as, especially, plasmid ColEl and its derivatives, for example pMB9, pSF2124, pBR317 or pBR322. Preferred vectors are derived from plasmid pBR322. Suitable vectors contain a complete replicon and a marker gene that renders possible the selection and identification of the microorganisms transformed with the expression plasmids by means of a phenotypic marker. Suitable marker genes impart to the microorganism, for example, resistance to heavy metals, antibiotics and the like. Furthermore, preferred vectors of the present invention contain apart from the replicon and marker gene regions recognition sequences for restriction endonucleases, so that the DNA sequence coding for the hirullin polypeptide and, where appropriate, the expression control sequence, can be inserted at those sites.

Several expression control sequences can be used to regulate the expression. The expression control sequences used are especially those of strongly expressed genes of the host cell that is to be transformed. In the case where pBR322 is used as the hybrid vector and $E.$ $coli$ is used as the host microorganism, suitable expression control sequences (which contain, inter alia, the promoter and the ribosomal binding site) are, for example, those of lactose operon, tryptophan operon, arabinose operon and the like, the promoter of the $\beta$-lactamase gene, and the phage $\lambda PL$ promoter, and others. Whereas the promoter of the $\beta$-lactamase gene ($\beta$-lac gene) is already contained in plasmid pBR322, the other expression control sequences must be inserted into the plasmid. Optionally, the expression control sequence is operably linked to a DNA sequence encoding a signal peptide operable in $E.$ $coli$ which in turn is linked in the proper reading frame to the hirullin gene.

Preferred hybrid vectors comprise a yeast promoter operably linked to a first DNA sequence encoding a signal peptide linked in the proper reading frame to a second DNA sequence encoding the hirullin polypeptide and a DNA sequence containing yeast transcription termination signals.

The yeast promoter is a regulated promoter such as the PHO5, ADH2 or GAL1 promoter, or a constitutive promoter. The constitutive yeast promoter is preferably derived from a highly expressed yeast gene, such as a gene encoding a glycolytic enzyme, such as the promoter of the enolase, glyceraldehyde-3-phosphate dehydrogenase (GAP) and 3-phosphoglycerate kinase (PGK) gene, furthermore the ADHL promoter and a shortened acid phosphatase PHO5 promoter which has been deprived of its upstream activation sites. Especially preferred is the GAP promoter and functional fragments thereof starting at nucleotide between $-550$ and $-180$, in particular at nucleotide $-540$, $-263$ or $-198$, and ending at nucleotide $-5$ of the GAP gene, and shortened constitutive PHO5 promoters starting at nucleotide between $-200$ and $-150$, in particular at $-173$, and ending at nucleotide $-9$ of the PHO5 gene.

The DNA sequence encoding a signal peptide ("signal sequence") is preferably derived from a yeast gene coding for a polypeptide which is ordinarily secreted. Yeast signal sequences are, for example, the signal and prepro sequences of the yeast invertase, $\alpha$-factor, pheromone peptidase (KEX1), "killer toxin" and repressible acid phosphatase (PHO5) genes and the glucoamylase signal sequence from $Aspergillus$ $awamori.$ Alternatively, fused signal sequences may be constructed by ligating part of the signal sequence (if present) of the gene naturally linked to the promoter used (for example PHO5), with part of the signal sequence of another heterologous protein. Those combinations are favoured which allow a precise cleavage between the signal sequence and e.g. the hirullin amino acid sequence. Additional sequences, such as pro- or spacer-sequences which may or may not carry specific processing signals can also be included in the constructions to facilitate accurate processing of precursor molecules. Alternatively, fused proteins can be generated containing internal processing signals which allow proper maturation in vivo or in vitro. For example, the processing signals contain a Lys-Arg residue, which is recognized by a yeast endopeptidase located in the Golgi membranes. The preferred signal sequences according to the present invention are those of the yeast PHO5 gene and of the yeast invertase gene.

A DNA sequence containing yeast transcription termination signals is preferably the 3' flanking sequence of a yeast gene which contains proper signals for transcription termination and polyadenylation. Suitable 3' flanking sequences are for example those of the yeast gene naturally linked to the promoter used. The preferred flanking sequence is that of the yeast PHO5 gene.

The yeast promoter, the optional DNA sequence coding for the signal peptide, the DNA sequence coding for the hirullin polypeptide and the DNA sequence containing yeast transcription termination signals are operably linked to each other, i.e. they are juxtaposed in such a manner that their normal functions are maintained. The array is such that the promoter effects proper expression of the hirullin gene (optionally preceded by a signal sequence), the transcription termination signals effect proper termination of transcription and polyadenylation and the optional signal sequence is linked in the proper reading frame to the hirullin gene in such a manner that the last codon of the signal sequence is directly linked to the first codon of the gene coding for the hirullin polypeptide and secretion of the hirullin polypeptide occurs. If the promoter and the signal sequence are derived from different genes, the promoter is preferably joined to the signal sequence between the major mRNA start and the ATG of the gene naturally linked to the promoter. The signal sequence should have its own ATG for translation initiation. The junction of these sequences may be effected by means of synthetic oligodeoxynucleotide linkers carrying the recognition sequence of an endonuclease.

Apart from the expression cassette, the yeast hybrid vectors according to the invention comprise a yeast replication origin. Accordingly, the hybrid vectors comprise a DNA segment originating from two-micron DNA containing the origin of replication or, if a two-micron DNA free strain of yeast is used, total two-micron DNA. The latter type of vectors is preferred. The preferred hybrid vectors according to the invention contain the complete two-micron DNA in a linearized form, i.e. two-micron DNA is cleaved once with a restriction endonuclease, the linearised DNA is linked with the other components of the vector prior to recircularization. The restriction site is chosen such that normal function of the REP1, REP2 and FLP genes and of the OR1, STB, IR1 and IR2 sites of two-micron DNA is maintained. Optionally, the restriction site is chosen such that the D gene of two-micron DNA is kept intact. Preferred restriction sites are the unique PstI site located within the D gene and the unique SnaBI site located outside of all said genes and sites.

Preferably, the yeast hybrid vectors according to the invention include one or more, especially one or two, selective genetic markers for yeast and such a marker and an origin of replication for a bacterial host, especially $Escherichia$ $coli.$ As to the selective gene markers for yeast, any marker gene can be used which facilitates the selection for transformants due to the phenotypic expression of the marker gene. Suitable markers for yeast are, for example, those expressing antibiotic resistance or, in the case of auxotrophic yeast mutants, genes which complement host lesions. Corresponding genes confer, for example, resistance to the antibiotics G418, hygromycin or bleomycin or provide for prototrophy in an auxotrophic yeast mutant, for example the URA3, LEU2, LYS2 or TRP1 gene.

As the amplification of the yeast hybrid vectors is conveniently done in *E. coli*, an *E. coli* genetic marker and an *E. coli* replication origin are included advantageously. These can be obtained from *E. coli* plasmids, such as pBR322 or a pUC plasmid, for example pUC18 or pUC19, which contain both *E. coli* replication origin and *E. coli* genetic marker conferring resistance to antibiotics, such as ampicillin.

The method for producing the yeast hybrid vectors according to the invention comprises linking the expression cassette comprising a yeast promoter operably linked to a DNA sequence coding for the hirullin polypeptide, and the DNA fragments containing selective genetic markers for yeast and for a bacterial host and origins of replication for yeast and for a bacterial host in the predetermined order.

Transformed host organisms

The invention relates likewise to host organisms transformed with a hybrid vector that contains a DNA sequence coding for a hirullin polypeptide, which DNA is controlled by an expression control sequence.

The process for the production of said host organisms comprises transforming a host organism with a hybrid vector containing a DNA sequence that codes for the hirullin polypeptide and that is regulated by an expression control sequence.

Suitable host organisms are, for example, the abovementioned microorganisms, especially strains of *Saccharomyces cerevisiae*. The transformation with the hybrid vectors of the invention is carried out, for example, in the manner described in the literature, for example for *S. cerevisiae* [A. Hinnen et al., Proc. Natl. Acad. Sci. USA 75, 1929 (1978)], *B. subtilis* (Anagnostopoulos et al., J. Bacteriol. 81, 741 (1961)] and *E. coli*. [M. Mandel et al., J. Biol. 53, 159 (1970)].

The preferred host organisms according to the invention are such strains of *S. cerevisiae* which lack certain peptidase activities such as peptidases A, B, Y, S and/or $\alpha$ activities. Such strains are known or can easily be prepared by introducing the desired single or multiple protease deficiency into the yeast genome by site-directed mutagenesis or gene-disruption or gene replacement [cf. H. Rudolph et al., Gene, 36 (1985) 87-95]. When the genomic sequence is known, as it is, for example, the case in protease yscB, carboxypeptidase yscY and carboxypeptidase ysc$\alpha$, the genomic protease gene can be made defective by insertion, substitution or deletion making use of the well-known site-directed mutagenesis procedure [see, for example, M. J. Zoller and M. Smith (1983) Methods Enzymol. 100, 468] which involves the preparation of an appropriately devised mutagenic oligodeoxyribonucleotide primer. Alternatively, the genomic protease gene can be replaced by foreign DNA or said foreign DNA can be inserted into a suitable restriction site of the protease gene.

As mentioned above, the preferred yeast strains according to the invention are devoid of endogenous two-micron DNA. Such cir° strains of *Saccharomyces cerevisiae* are known or can be prepared by methods known in the art [see, for example, C. P. Hollenberg (1982) Curr. Top. Microbiol. Immun. 96, 119]. The following alternative procedure for the preparation of cir° strains is based on the presumption that curing of the two-micron plasmid by a second plasmid involves increasing the dosage of the STB site to titrate out the REP1 and REP2 proteins. This relative reduction of the REP1 and REP2 proteins would lead to an instability of the endogenous two-micron plasmid.

Preferably, the second plasmid used has a defect in or lacks the REP1 gene. An example of such a plasmid is pDP38 which apart from the REP1 gene lacks one of the inverted repeat (IR2) structures. This makes its high copy number expression dependent on the complementation of REP1 protein by the endogenous two-micron plasmid. It contains two yeast selective markers: URA3, used in both high and low copy number situations, and dLEU2, applicable only in high copy number systems [E. Erhart et al. (1968) J. Bacteriol. 625].

A yeast strain which is Ura$^-$ and Leu$^-$ is transformed with plasmid pDP38 and selected for Ura$^+$ colonies. The selection on uracile free plates (Ura selection) gives a much better transformation frequency than the selection on leucine free plates (Leu selection), as the URA3 gene is much better expressed than the defective dLEU2 gene. A single colony is selected and streaked onto a Leu selection plate which gives colonies of varying sizes and form. Some of the smallest colonies are restreaked onto Ura selection plates and replica-plated onto Leu selection plates. Those colonies are selected that can grow under Ura selection but only very slowly under Leu selection. Growth on Ura selection plates shows that the plasmid pDP38 is still present and that the merely slow growth under Leu selection is not due to the loss of this plasmid, and the failure of growth under Leu selection implies that pDP38 is not able to complement this marker. The latter fact can be explained in two ways: A. The LEU2 gene on pDP38 is mutated, or B: The plasmid cannot complement leu2 because it cannot raise its copy number, implying that the two-micron plasmid is not available (i.e. lost) to complement the REP1 gene product. These two possibilities can be distinguished very easily. In the first case, the minimal growth seen with said colonies (as against the absolute zero growth of cells without pDP38) shows that some LEU2 expression is present. The second point can be directly tested, as in the absence of the two-micron plasmid pDP38 will act only as an ARS type plasmid, i.e. it will be very unstable so that most of the colonies will lose it after a few generations. Accordingly, when a single colony is streaked onto a YPD plate, and single colonies taken and replica-plated onto uracile free plates, then only a few will grow under Ura selection. Non growing colonies are checked by hybridization for pUC and two-micron sequences. Colonies which show no hybridization signals are free of plasmid pDP38 and of endogenous two-micron plasmids (cir° strains).

Cultivation of the transformed host organisms

The transformed host strains are cultured using methods known in the art.

Thus, the transformed host strains, such as *S. cerevisiae* or *E. coli* strains, according to the invention are cultured in a liquid medium containing assimilable sources of carbon, nitrogen and inorganic salts.

Various carbon sources are usable. Example of preferred carbon sources are assimilable carbohydrates, such as glucose, maltose, mannitol, fructose or lactose, or an acetate such as sodium acetate, which can be used either alone or in suitable mixtures. Suitable nitrogen sources include, for example, amino acids, such as casamino acids, peptides and proteins and their degradation products, such as tryptone, peptone or meat extracts, furthermore yeast extract, malt extract, corn steep liquor, as well as ammonium salts, such as ammonium chloride, sulphate or nitrate which can be used either alone or in suitable mixtures. Inorganic salts which may be used include, for example, sulphates, chlorides, phosphates and carbonates of sodium, potassium, magnesium and calcium. Additionally, the nutrient medium may also contain growth promoting substances. Substances which promote growth include, for example, trace elements, such as iron, zinc, manganese and the like, or individual amino acids.

Furthermore, the medium contains, for example, growth-promoting substances, such as trace elements, for example iron, zinc, manganese and the like, and preferably substances that exert a selection pressure and prevent the growth of cells that have lost the expression plasmid. For example ampicillin is added to the medium when an *E. coli* expression plasmid contains an amp ® gene. Such an addition of antibiotically active substances also has the effect of killing contaminating microorganisms that are sensitive to antibiotics.

Yeast hybrid vectors comprising the complete two-micron DNA (including a functional origin of replication) are stably maintained within strains of *Saccharomyces cerevisiae* which are devoid of endogenous two-micron circles (so-called cir° strains) so that the cultivation can be carried out under non-selective growth conditions, i.e. in a complex medium.

Host cells containing hybrid plasmids with a constitutive promoter (e.g. yeast ADH1, GAP) express the DNA encoding the hirullin controlled by said promoter without induction. However, if said DNA is under the control of a regulated promoter (e.g. yeast GALT or PH05) the composition of the growth medium has to be adapted in order to obtain maximum levels of MRNA transcripts, i.e. when using the yeast PH05 promoter the growth medium must contain a low concentration of inorganic phosphate for derepression of this promoter.

The cultivation is carried out by employing conventional techniques. The culturing conditions, such as temperature, pH of the medium and fermentation time are selected in such a way that maximal levels of the hirullin are produced. A chosen *E. coli* or *S. cerevisiae* host strain is preferably grown under aerobic conditions in submerged culture with shaking or stirring at a temperature of about 25° to 40° C., preferably at about 30° C., at a pH value of from 4 to 7, for example at approximately pH 5, and for at least 1 to 3 days, preferably until satisfactory yields of protein are obtained.

The hirullin polypeptides expressed by the host cells can be accumulated inside the cells or can be secreted into the culture medium depending on the gene construct (i.e. whether a signal sequence is included) and the host used.

If the hirullin polypeptide is secreted into the culture medium it can be isolated therefrom by conventional means. For example, the first step consists usually in separating the cells from the culture fluid by means of centrifugation. The resulting supernatant can be enriched for hirullin polypeptides by treatment with polyethyleneimine so as to remove most of the non-proteinaceous material, and precipitation of the proteins by saturating the solution with ammonium sulphate. A further enrichment of the hirullin polypeptide can be achieved by extracting the acetic acid supernatant with n-butanol. Other purification steps include, for example, desalination, chromatographic processes, such as ion exchange chromatography, gel filtration chromatography, partition chromatography, HPLC, reversed phase HPLC and the like. The separation of the constituents of the protein mixture is also effected by dialysis, according to charge by means of gel electrophoresis or carrier-free electrophoresis, according to molecular size by means of a suitable Sephadex column, by affinity chromatography, for example with antibodies, especially monoclonal antibodies, or with thrombin coupled to a suitable carrier for affinity chromatography, or by other processes, especially those known from the literature. In principle, the same techniques used to isolate the hirullins from *H. manillensis* extracts can be applied.

If the hirullin polypeptide is not secreted or if it is desired to isolate any additional hirullin polypeptide which is cell associated, i.e. which bas accumulated intracellularly or in the periplasmic space, some supplementary purification steps are required. Thus, in case the hirullin polypeptide has accumulated within the cells, the first step for the recovery thereof consists in liberating it from the cell interior. In most procedures the cell wall is first removed by enzymatic digestion with glucosidases. Subsequently, the resulting spheroplasts are treated with detergents, such as Triton. Alternatively, mechanical forces, such as shearing forces (for example X-press, French-press) or shaking with glass beads, are suitable for breaking cells. In the case where the hirullin polypeptide is secreted by the host cells into the periplasmic space, a simplified protocol can be used: The heterologous protein is recovered without cell lysis by enzymatic removal of the cell wall or by treatment with chemical agents, e.g. thiol reagents or EDTA, which give rise to cell wall damages permitting the product to be released.

Depending on the method employed, the compounds of the formulae I and II are obtained in the free form or in the form of acid addition salts, inner salts or salts with bases. The free compound can be obtained in a known manner from the acid addition salts. In turn, therapeutically acceptable acid addition salts can be obtained from the free compounds by reaction with acids, e.g. with those acids which form the above-mentioned salts, and by evaporation or lyophilisation. The inner salts can be obtained by adjusting the pH to a suitable neutral point.

Pharmaceutical compositions

The novel hirullins according to the present invention have valuable pharmacological properties and can be used prophylactically or, especially, therapeutically.

The hirullin compounds according to the invention are specific inhibitors of thrombin while exhibiting no interactions with other proteinases of the blood coagulation system. The active toxicity is extremely low. Similarly, no hypersensitivity reactions or allergic reactions are observed.

The novel hirullin compounds according to the invention can therefore be used for the therapy and prophylaxis of thromboses and thromboembolisms, including the prophylaxis of post-operative thromboses, for acute shock therapy (for example for septic or polytraumatic shock), for the therapy of consumption coagulopathies, in haemodialyses, haemoseparations and in extracorporeal blood circulation.

The invention relates also to pharmaceutical compositions that contain at least one of the compounds according to the invention or a pharmaceutically acceptable salt thereof, optionally together with a pharmaceutically acceptable carrier and/or adjuncts.

The compositions can be used especially in the above-mentioned indications, when they are administered, for example, parenterally, such as intravenously, intracutaneously, subcutaneously or intramuscularly, or topically.

The invention relates also to the use of the novel compounds according to the invention and to pharmaceutical compositions containing them for the prophylactic and therapeutic treatment of the human or animal body, especially for the above-mentioned clinical syndromes, especially for inhibiting the coagulation of blood inside and outside the human or animal body.

The dosage depends especially on the specific form of administration and on the purpose of the therapy or prophylaxis. The size of the individual doses and the administration regime can best be determined by way of an individual judgement of the particular case of illness; the methods of determining relevant blood factors required for this purpose are familiar to the person skilled in the art. Normally, in the case of an injection the therapeutically effective amount of the compounds according to the invention is in a dosage range of from approximately 0.005 to approximately 0.1 mg/kg body weight. A range of from approximately 0.01 to approximately 0.05 mg/kg body weight is preferred. The administration is effected by intravenous, intramuscular or subcutaneous injection. Accordingly, pharmaceutical compositions for parenteral administration in single dose form contain per dose, depending on the mode of administration, from approximately 0.4 to approximately 7.5 mg of the compound according to the invention. In addition to the active ingredient these pharmaceutical compositions usually also contain a buffer, for example a phosphate buffer, which is intended to keep the pH value between approximately 3.5 and 7, and also sodium chloride, mannitol or sorbitol for adjusting the isotonicity. They may be in freeze-dried or dissolved form, it being possible for solutions advantageously to contain an antibacterially active preservative, for example from 0.2 to 0.3% 4-hydroxybenzoic acid methyl ester or ethyl ester.

A composition for topical application can be in the form of an aqueous solution, lotion or gel, an oily solution or suspension or a fat-containing or, especially, emulsified ointment. A composition in the form of an aqueous solution is obtained, for example, by dissolving the active ingredients according to the invention, or a therapeutically acceptable salt thereof, in an aqueous buffer solution of from pH 4 to pH 6.5 and, if desired, adding a further active ingredient, for example an antiinflammatory agent, and/or a polymeric binder, for example polyvinylpyrrolidone, and/or a preservative. The concentration of active ingredient is from approximately 0.1 to approximately 1.5 mg, preferably from 0.25 to 1.0 mg, in 10 ml of a solution or 10 g of a gel.

An oily form of administration for topical application is obtained, for example, by suspending the active ingredient according to the invention, or a therapeutically acceptable salt thereof, in an oil, optionally with the addition of swelling agents, such as aluminium stearate, and/or surfactants (tensides) having an HLB value ("hydrophilic-lipophilic balance") of below 10, such as fatty acid monoesters of polyhydric alcohols, for example glycerin monostearate, sorbitan monolaurate, sorbitan monostearate or sorbitan monooleate. A fat-containing ointment is obtained, for example, by suspending the active ingredient according to the invention, or a salt thereof, in a spreadable fatty base, optionally with the addition of a tenside having an HLB value of below 10. An emulsified ointment is obtained by triturating an aqueous solution of the active ingredient according to the invention, or a salt thereof, in a soft, spreadable fatty base with the addition of a tenside having an HLB value of below 10. All these forms for topical application can also contain preservatives. The concentration of active ingredient is from approximately 0.1 to approximately 1.5 mg, preferably from 0.25 to 1.0 mg, in approximately 10 g of base.

In addition to the compositions described above and pharmaceutical compositions analogous thereto that are intended for direct medicinal use in the body of a human or a mammal, the present invention relates also to pharmaceutical compositions and preparations for medicinal use outside the living body of humans or mammals. Such compositions and preparations are used especially as anticoagulant additives to blood that is being subjected to circulation or treatment outside the body (for example extracorporeal circulation or dialysis in artificial kidneys), preservation or modification (for example haemoseparation). Such preparations, such as stock solutions or alternatively preparations in single dose form, are similar in composition to the injection preparations described above; however, the amount or concentration of active ingredient is advantageously based on the volume of blood to be treated or, more precisely, on its thrombin content. In this connection it must be borne in mind that the active ingredient according to the invention (in free form) completely deactivates approximately 5 times the amount by weight of thrombin, are physiologically harmless even in relatively large amounts, and are eliminated from the circulating blood rapidly even in high concentrations so that there is no risk of overdose, even, for example, during transfusions. Depending on the specific purpose, the suitable dose is from approximately 0.01 to approximately 1.0 mg of the active ingredient/liter of blood, although the upper limit may still be exceeded without risk.

The invention relates especially to the hirullins, DNAS, hybrid vectors, transformed host organisms and to the processes for their manufacture as described in the Examples.

BRIEF DESCRIPTION OF THE DRAWINGS

In the following experimental part various embodiments of the present invention are described with reference to the accompanying drawings in which:

FIGS. 1 and 2 are schematic diagrams showing the in vitro synthesis of the hirullin P6 and P18 genes including the PH05 signal sequence with the preferred yeast codons. The 12 oligodeoxynucleotides used are indicated by numbered full lines and dotted lines, respectively.

EXPERIMENTAL PART

Example 1

Figure 3:
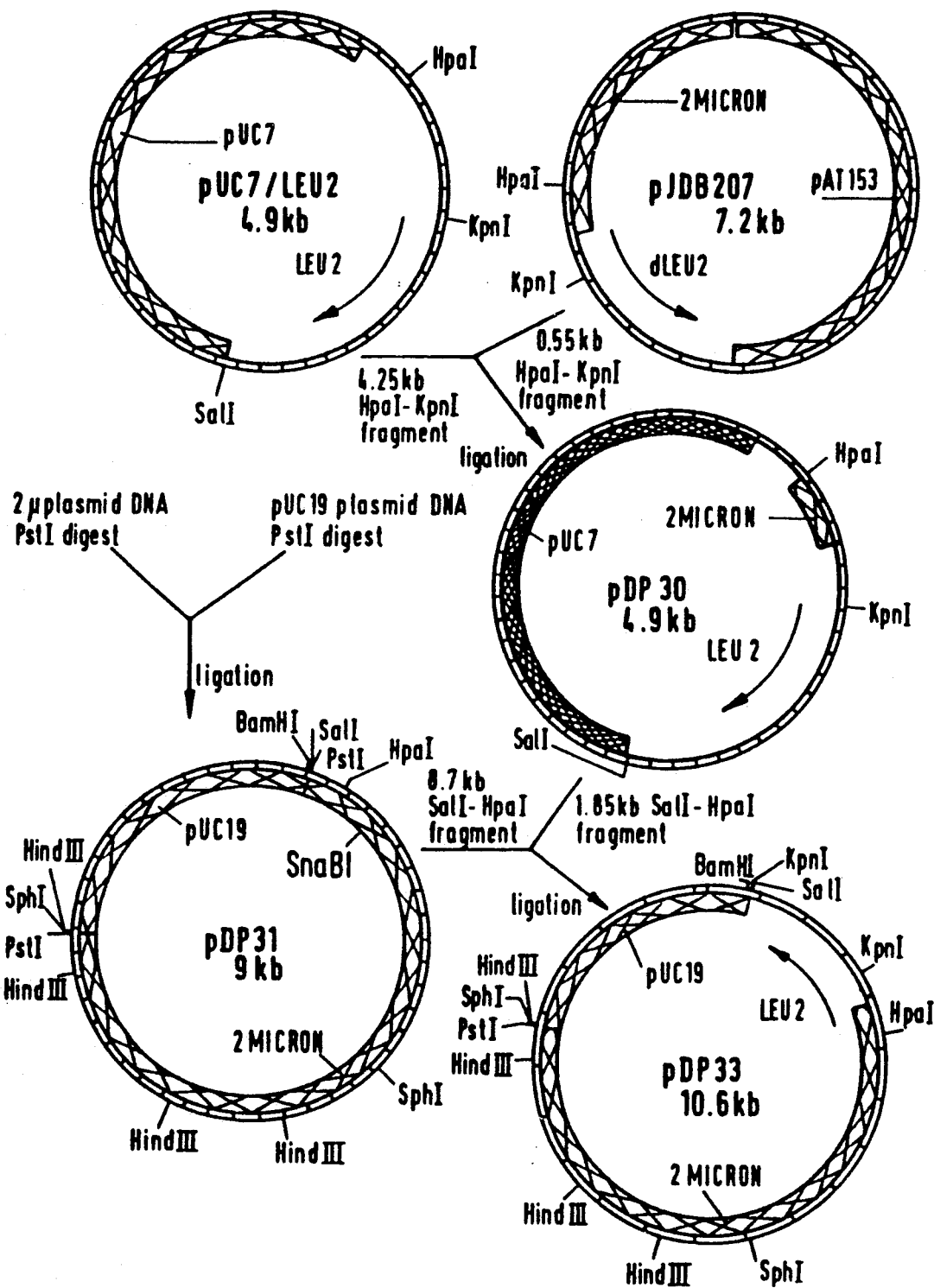
FIG. 3 schematically illustrates the construction of plasmid pDP33.

Production of crude extract 30 kg of frozen leeches *Hirudinaria manillensis* (occurring and collected in China) are ground with a blade-homogenizer. The extraction is carried out as described by Bagdy et al. [Thromb. Res. 2, 229 (1973)]. 90 liters of cold 80% v/v acetone are added to the leech slurry and the mixture is stirred at 0° C. for 15 min. Insoluble proteins precipitate after addition of NaCl to a final concentration of 0.4M and trichloroacetic acid (TCA) to a final concentration of 0.4M under constant stirring for 60 min. The insoluble proteins are separated by decantation and discarded. The extraction step is repeated with the supernatant. This time, 30 liters of cold 80% (v/v) acetone containing NaCl and TCA are used. Crude hirullin is precipitated by adding two volumes of cold acetone to the extract at −10° C. After centrifugation the precipitate is washed with cold acetone and lyophilized.

Example 2

Purification of crude extract 1 g crude extract is dissolved in 20 ml 0.1M acetic acid, centrifuged and the clear supernatant is applied onto a Sephadex G50 superfine column (Pharmacia 100 cm × 26 mm; 400 ml bed volume) preequilibrated with 0.1M acetic acid and connected to a Pharmacia FPLC system. The elution is carried out with 0.1M acetic acid at a flow rate of 0.2 ml/min and monitored at 280 nm. 6 ml fractions are collected and tested for activity with a thrombin inhibition assay as described by S. Mao et al. [Anal. Bioch. 161, 514 (1987)). This step gives a 4-fold purification. The active fractions are dried on a lyophilizer, redissolved in 2 ml 0.02M histidine/HCl pH 5.6 (=eluent A), centrifuged and the clear supernatant applied onto a Q Sepharose fast flow anion exchanger column (Pharmacia, 40 cm × 16 mm; bed volume 66 ml) connected to a pharmacia FPLC system and preequilibrated with eluent A. Elution is done with a step gradient at a flow rate of 2 ml/min: 48 min 0% B ( eluent B: 0.02M histidine/HCl pH 5.6+1M NaCl ), 102 min 15% B, 65 min 100% B. The run is monitored at 280 nm and the active fractions are pooled and desalted on a Sephadex G50 fine column with 0.01M $NH_4HCO_3$, then freeze-dried. This step yields a 6-fold purification.

The dried material is now submitted to separation of isoforms as described in the following example.

Example 3

Final purification and separation of isoforms

The dried material is dissolved in bidistilled water at a concentration of 9 mg/200 µl 200 µl portions are applied onto a Nucleosil C18 RP HPLC column, 8 × 250 mm, 7 µm particle size, AUFS 2 at 214 nm, flow 5 ml/min. Eluent A: 0.1% trifluoroacetic acid, eluent B: acetonitril+0.08% trifluoroacetic acid. Monitor 214 nm. Gradient table:

| time [min] | % B |
|---|---|
| initial | 10 |
| 2 | 10 |
| 4 | 18 |
| 44 | 28 |
| 46 | 90 |
| 51 | 90 |
| 54 | 10 |
| 64 | 10 |

Single peak fractions are manually collected and immediately dried on a vacuum centrifuge. An aliquot (10 µl) is 1:1000 diluted and tested for antithrombin activity. The active fractions are rechromatographed under the same conditions.

The two most abundant peak fractions are chosen (designated hirullin P6 and hirullin P18) and submitted to the next purification step on a Vydac 219 TP phenyl silica RP HPLC column (4.6×150 mm; 5 µm pores). Flow rate 1 ml/min, eluents and gradient are as before. Up to 700 µg protein can be applied onto the column. The fractions are collected and immediately dried on a vacuum centrifuge.

The last purification step is carried out on a Pharmacia FPLC system with an anion exchanger column (Mono Q, 5×50 mm
Eluent A: 0.05M $HCOONH_4$ pH 5.1
Eluent B: 0.05M HCOOH, flow rate 1.5 ml/min.
The peak fraction to be purified is dissolved in 1 ml eluent A and applied onto the column.

| Monitor: 280 nm. Elution gradient: | |
|---|---|
| time [min] | % B |
| initial | 0 |
| 6 | 0 |
| 36 | 100 |
| 40 | 100 |
| 42 | 0 |
| 52 | 0 |

The fractions are collected and dried on a vacuum centrifuge. The obtained solid consists of pure hirullin (purity about or more than 99%).

TABLE 1

| Yields of final purification | |
|---|---|
| step | total protein |
| amount to be purified | 129 mg |
| C18 RP HPLC | 2 mg hirullin P6 |
|  | 0.5 mg hirullin P18 |
| Phenyl RP HPLC | 1.3 mg hirullin P6 |
|  | 0.28 mg hirullin P18 |
| Mono Q | 0.328 mg pure hirullin P6 |
|  | 0.128 mg pure hirullin P18 |

Example 4

Characterization of hirullins a) Retention times of Mono Q column

Conditions: see example 2
hirullin P6 28.6 min
hirullin P18 30.1 min b) Retention times on phenyl RP HPLC column Conditions: see example 2
hirullin P6 16.4 min
hirullin P18 24.75 min c) Amino acid analysis of the whole molecules Approximately 1.5 µg of each isoform is hydrolysed for 24 h with 6M HCl at 110° C. and then analysed as described by R. Knecht [Anal. Chem. 58, 2375 (1986)]. The hydrolysates have the following composition:

| amino acid | P6 | P18 |
|---|---|---|
| Asp + Asn | 7.8 (8) | 10.7 (10) |
| Glu + Gln | 13.3 (13) | 9.9 (9) |
| Ser | 4.1 (4) | 6.5 (6) |
| Thr | 3.2 (2)* | 4.5 (3)* |
| Gly | 7.8 (8) | 9.6 (9) |
| Ala | 2.4 (1) | 1.6 (0) |
| Arg | 3.2 (3) | 1.3 (1) |
| Pro | 2.8 (3) | 2.2 (2) |
| Val | 2.2 (2) | 2.5 (2) |
| Met | 1.8 (1) | 1.9 (1) |
| Ile | 2.2 (2) | 1.3 (1) |
| Leu | 1.2 (1) | 2.5 (2) |
| Phe | 2.3 (2) | 3.7 (3) |
| Cys | 5.4 (6) | 5.5 (6) |
| Lys | 3.7 (3) | 3.7 (3) |
| His | 1.2 (1) | 1.2 (1) |
| Tyr | 2.6 (2) | 2.6 (2) |
| total | 63 | 62 |

Values in brackets and the total number of amino acids are derived from sequencing data (see Example 4g).
*The O-glycosylated Thr residues do not appear in the sequencing data.

d) Amino acid analysis of fragments

Hirullin P6: Fragementation: 200 µg hirullin P6 are oxidized with 50 µl freshly prepared performic acid during 2 hours at −4° C. After addition of 100 µl water the sample is lyophilized, then dissolved in 50 µl 0.1M NH₄HCO₃ buffer. 5 µg endoproteinase Lys-C in 150 µl 0.1M NH₄HCO₃ are added. After 5 hours the hydrolysis is stopped with 5 µl acetic acid. The fragments are separated by HPLC and analysed as described by R. Knecht (supra).

| Fragment | P6 1-36 | P18 37-63 |
|---|---|---|
| Asp + Asn | 5 (5) | 3 (3) |
| Glu + Gln | 6 (6) | 6 (7) |
| Ser | 3 (3) | 1 (1) |
| Thr | 2 (2) | 1 (0)* |
| Gly | 5 (5) | 3 (3) |
| Ala | 2 (1) | 0 (0) |
| Arg | 2 (2) | 1 (1) |
| Pro | 0 (0) | 3 (3) |
| Val | 1 (1) | 1 (1) |
| Met | 1 (1) | 0 (0) |
| Ile | 1 (1) | 1 (1) |
| Leu | 0 (0) | 1 (1) |
| Phe | 2 (1) | 1 (1) |
| Cys | 6 (5) | 1 (1) |
| Lys | 2 (2) | 1 (1) |
| His | 0 (0) | 1 (1) |
| Tyr | 1 (1) | 1 (1) |

Values in brackets are derived from sequencing data (see Example 4g).
*The O-glycosylated Thr$^{43}$ residue does not appear in the sequencing data.

Hirullin P18: Fragmentation: 20pg hirullin P18 are oxidized as described with hirullin P6. The oxidized polypeptide is dissolved in 50 µl 0.1M NH₄HCO₃ buffer and 2 µl thermolysin solution containing 1 µg enzyme is added. The sample is digested overnight at 37° C. The fragments are separated by HPLC and analysed as described by R. Knecht (supra).

| P18 fragment | 1-13 | 14-35 | 36-53 | 36-56 | 57-62 |
|---|---|---|---|---|---|
| Asp + Asn | 2 (2) | 4 (4) | 2 (2) | 2 (2) | 2 (2) |
| Glu + Gln | 1 (1) | 2 (2) | 3 (3) | 4 (4) | 2 (2) |
| Ser | 2 (2) | 1 (1) | 2 (2) | 3 (3) | |
| Thr | 2 (2) | | 2 (1)* | 2 (1)* | |
| Gly | 1 (1) | 4 (5) | 2 (3) | 2 (3) | |
| Arg | | | 1 (1) | 1 (1) | |
| Pro | | | 2 (2) | 2 (2) | |
| Val | 1 (1) | | 1 (1) | 1 (1) | |
| Met | | 1 (1) | | | |
| Ile | | | | | 1 (1) |
| Leu | | 1 (1) | | | 1 (1) |
| Phe | | 1 (1) | 1 (1) | 2 (2) | |
| Cys | 3 (2) | 6 (4) | | | |
| Lys | | 2 (2) | 1 (1) | 1 (1) | |
| His | | 1 (1) | | | |
| Tyr | 2 (2) | | | | |

Values in brackets are derived from sequencing data (see Example 4g).
*The O-glycosylated Thr$^{46}$ residues do not appear in the sequencing data.

e) Molecular weight determination by $^{252}$Cf plasma desorption time of flight mass spectrometry Hirullin P6: Molecular weight 7415.9 daltons
P6 fragment 37-63:
The sugar chain will be derived from fragment 37-63. The following molecular weights are obtained:

| mass | fragment |
|---|---|
| 3326.3 | P6 37-63 + SNAc |
| 3406.4 | + SNAc + sulfate |
| 3488.4 | + SNAc + S |
| 3568.5 | + SNAc + S + sulfate |
| 3634.4 | + SNAc + S + fucose |
| 3714.5 | + SNAc + S + fucose + sulfate |

The mass spectrometric data show that Thr$^{43}$ carries an O-glycosyl radical of the formula —SNAc—S—Fuc or, partially, —SNAC—S in which SNAc is N-acetyl-galactosamine or N-acetylglucosamine, S is galactose, mannose or glucose and Fuc is fucose.

Hirullin P18: Molecular weight 7198.6 daltons
P18 fragment 36-53:
Partial removal of the sugars (see Example 6) and mass spectrometric determination show that Thr$^{46}$ carries an O-glycosyl radical of the formula —S-NAc—S—Fuc in which the abbreviations have the meanings given above.

The exact nature of the radicals SNAc and S has not yet been determined.

f) Thrombin-hirullin inhibition constants

Determination with human alpha-thrombin according to the method of S. R. Stone and J. Hofsteenge [Biochemistry 25, 4622 (1986)] gives the following inhibition constants $K_i$:
P6: $K_i = 58 \pm 2$ fM
P18: $K_i = 7.8 \pm 1$ pM g) Sequence analysis of hirullins P6 and P18

The amino acid sequence is determined by automatic solid-phase Edman degradation of the intact reduced and alkylated molecule and of a C-terminal fragment thereof.

Reduction and alkylation of hirullins P6 and P18, 50 µg protein are dissolved in 250 µl buffer pH 8.6 6M guanidine/HCl, 0.5M Tris, 0.2% EDTA) and 5 mg dithiothreitol.

The reaction mixture is flushed with nitrogen and kept for 6 h at 75° C. Then 3 µl vinylpyridine are added and shaked for 2 h in the dark. The reaction mixture is desalted by gelfiltration and dried on a vacuum centrifuge.

0.5 nmoles are subjected to sequence analysis on a gas-phase sequencer (model 477A and PTH-analyzer model 120A by Applied Biosystems) according to the manufacturer's protocol. 35 to 45 residues can be homogenously sequenced.

Fragmentation of hexakis-(pyridylethyl)-P6 with endoproteinase Lys-C: Overnight digestion at a substrate-enzyme ratio 20:1 (w/w) in 0.1M 4-etbylmorpholin acetate buffer pH 8.1 at room temperature. 100 pmoles of the C-terminal fragment give a homogenous sequence up to residue 62.

Fragmentation of bexakis-(pyridylethyl)-P18 with cyanogenbromid [cf. Practical Protein Chemistry (A. Darbre, ed.), J. Wiley and Sons 1986] and with endoproteinase Lys-C yield C-terminal overlapping fragments.

Sequences of P6 and P18:

P6 MRYTACTESGQNQCICEGNDVCGQGRNCQFDSSGKKCVEGEGT*RKPQNEGQHDFDPIPEEYLS

P18 VSYTDCTSGQNYCLCGGNFCGDGKHCEMDGSENKCVDGEGTPKRQT*SGPSDFEEFSLDDIEQ wherein T* is O-glycosylated threonine as evidenced by amino acid analysis and mass spectrometric data (see Example 4e).

$$SO_3H$$ (above T* in P6 sequence)

Example 5

Removal of the sulfate monoester group from hirullin P6

The biological activity is determined from the inhibition of thrombin, whose enzymatic activity is in turn determined using the chromogenic substrate Chromozym TH (a product of Boehringer, Mannheim, West Germany, for thrombin and hirudin determination) in accordance with known directions supplied with the test preparation.

Arylsulfatase (ARS) from *Helix pomatia* (a product of Boehringer, Mannheim, West Germany), 5 IU/mg. The enzymatic activity is determined by the known method of Leon et al. Biochem. J. 75, 612–617], using the chromogenic substrate p-nitrophenol sulfate (1.8 mm/l in the batch).

Desulfation (1) Preliminary experiment (for determining the optimum ARS concentration)

(a) the following stock solutions are prepared:
(A) Hirullin P6 solution having a concentration of 2 mg/ml, obtained by dissolving hirullin P6 in solution (C).
(B) Arylsulfatase solution with a concentration of 1.25 mg/ml: by mixing 25 parts of the commercially available suspension with 100 parts of solution (C).
(C) Buffer solution: 0.1M aqueous solution of pyridine acetate, pH 5.4.

(b) Procedure

A series of samples is obtained by mixing the following components: each sample contains 15 μl of solution A (corresponding to 30 μg of hirullin) and 10 μl of solution B (corresponding to 12.5 μg of arylsulfatase) or of a solution in which the concentration of the enzyme is adjusted to ½, ¼, ⅛, 1/16 and 1/32 of the original concentration by diluting solution B with the buffer C. Each sample of 25 μl is incubated for 60 min at 25° C., then heated for 3 min to 100° C. to denature the sulfatase, rapidly cooled, and analysed for content of free and sulfated tyrosine (in accordance with the method described below).

(2) Preparatory process 15 parts by volume of solution A are mixed with 10 parts by volume of a dilute solution B, whose optimum lowest possible concentration of each solution was determined in the preliminary experiment and adjusted by diluting stock solution B with the buffer solution C. The mixture is incubated at 25° C. for about 30–60 minutes, heated briefly (e.g. under conditions of flash sterilisation) to 100° C. and immediately cooled in order to denature the desulfating enzyme. The reaction mixture is separated through a column of Sephadex ® G50 or G75, CM-Sephadex ®, Wofatit ® CP, Amberlite ® IRC or another equivalent cation exchanger, if desired after concentrating the reaction mixture in vacuo at or below room temperature. If required, this separation is repeated until desulfatohirullin P6 of the desired purity (determined e.g. by the inhibitory test with thrombin and/or amino acid analysis) is obtained. The product in solid form is obtained by lyophilising the corresponding solutions (eluates). According to the amino acid analysis (by C-terminal proteolysis), the pure product is free from tyrosine O-sulfate and exhibit the full activity of hirullin P6 in the inhibitory activity test on thrombin (e.g. with Chromozym TH, see above).

Example 6

Removal of O-linked sugar residues from hirullins P6 and P18

200 μg polypeptide is dissolved in 30 μl freshly prepared mixture of anisole/trifluoromethanesulfonic acid (1 ml:2 ml) and kept for 3 hours in ice-water under occasional shaking. Then the solution is neutralized by adding 300 μl 2.5% ammonia. Anisole is removed by extracting four times with 20 μl dichloromethane. The removal is monitored with time of flight mass spectrometry. Separation of glycosylated from free peptide is carried out by HPLC. The deglycosylated hirullins are characterised by mass spectrometry (cf. Example 4e):
deglycosylated desulphatohirullin P6: det. 6972.9 (calc. 6970.6)
deglycosylated hirullin P18: det. 6687.7 (calc. 6687.05)

Example 7

In vitro synthesis of the hirullin P6 and hirullin P18 genes with preferred yeast codons The coding sequences of the hirullin expression cassettes are devised with preferred yeast codons [B. Hall, J. Biol. Chem. 257 (1982) 3026] to guarantee optimal translation of the hirullin mRNAs. The coding sequences contain the PH05 signal sequence fused in frame to the coding sequence of hirullin P6 and hirullin P18, respectively. The 5' ends of the synthetic DNAs contain the sticky ends of the EcoRI restriction site. At the 3' end the stop codon TAG is immediately followed by the sticky ends of the BamHI site. The sequence of the 251 bp EcoRI-BamHI DNA fragment of hirullin P6

(HTI-P6) is shown in FIG. 1. The sequence of the 248 bp EcoRI-BamHI DNA fragment of hirullin P18 (HTI-P18) is given in FIG. 2.

FIGS. 1 and 2 also indicate the strategy for the in vitro synthesis of the double-stranded DNA. 12 oligodeoxynucleotides each are synthesized using the phosphor-amidite method [M. H. Caruthers, in: Chemical and Enzymatic Synthesis of Gene Fragments (H. G. Gassen and A. Lang, Eds.), Verlag Chemie, Weinbeim, FRG] on an Applied Biosystems Model 380B synthesizer. The sequence of the individual oligonucleotides is shown in FIG. 1 and FIG. 2. The overlaps are unique. The lyophilized oligonucleotides are redissolved in 50 mM Tris-HCl pH 8.0 at a concentration of 10 pmoles/$\mu$l. 10 pmoles each of the 12 oligonucleotides are mixed. The oligonucleotides are phosphorylated in 20 $\mu$l of 25 mM Tris-HCl pH 8.0, 10 mM MgCl$_2$, 10 mM NaCl, 3 mM DTT, 0.4 mM ATP and 8 units of polynucleotide kinase (Boehringer) for 1 h at 37° C. After 30 min at room temperature the mixture is heated for 5 min at 95° C. in a waterbath and allowed to cool slowly to room temperature in the waterbath overnight. The annealed oligonucleotide mixture is then stored on ice.

Plasmid pUC19 (Biolabs) is cut to completion with EcoRI and BamHI. The large, 2.7 kb fragment is isolated on a preparative 0.6% agarose gel. The DNA is recovered by electroelution, purified by DE52 ion exchange chromatography and ethanol precipitation. The DNA is redissolved in H$_2$O at a concentration of 0.4 pmoles/$\mu$l.

20 $\mu$l of the annealed oligonucleotide mixture (10 pmoles each of oligonucleotides 1-12), 0.4 pmoles of the 2.7 kb EcoRI-BamHI fragment of pUC19 and 400 units of T4 DNA ligase (Biolabs) are incubated for 16 h at 15° C.

10 $\mu$l aliquots are used to transform competent E. coli JM109 Ca$^{++}$ cells. Cells are plated onto LB agar plates supplemented with 100 $\mu$g/ml of ampicillin, 7 $\mu$g/ml of isopropyl-$\beta$-D-thio-galactopyranoside (IPTG) and 30 $\mu$g/ml of 5-bromo-4-chloro-3-indolyl-$\beta$-galactoside (XGAL). 12 transformed, ampicillin resistant white colonies are grown individually in LB medium containing 100 $\mu$g/ml of ampicillin. Plasmid DNA is prepared by the method of Holmes et al. [Anal. Biochem. 114 (1981) 193] and analysed by EcoRI and BamHI restriction digests. Plasmid DNAs with the 251 bp or 248 bp EcoRI-BamHI insert are further analysed by DNA sequencing on both strands. One clone each with the correct sequence on both DNA strands is selected and referred to as pUC19/HTI-P6 for hirullin P6 and pUC19/HTI-PI8 for hirullin P18, respectively.

Example 8

Construction of plasmid pJDB207/GAPFL-HTI-P6 pJDB207/GAPFL-HTI-P6 is a yeast plasmid for the expression of hirullin P6 under the control of a short, constitutive promoter of the yeast glyceraldehyd-3-phosphate dehydrogenase (GAPDH) gene. The coding sequence (HTI-P6) of hirullin P6 consists of preferred yeast codons.

10 $\mu$g of plasmid pUC19/HTI-P6 are digested with restriction endonucleases BamHI and EcoRI. The 251 bp EcoRI-BamHI fragment is separated from other DNA fragments on a 1.2% preparative agarose gel. The DNA bands are stained by ethidiumbromide and visualized under UV light at 360 nm. The 251 bp DNA band is cut from the gel and electroeluted in 0.2× TBE buffer (TBE: 90 mM Tris-base, 90 mM boric acid, 2.5 mM EDTA, pH 8.3) for 45 min at 100 mA. After changing polarity for 45 sec, the DNA solution is collected and adjusted to 0.15M NaCl. The DNA is adsorbed to a 100 $\mu$l bed of DE52 ion exchanger (Whatman) and eluted in 400 $\mu$l of high salt buffer (10 mM Tris-HCl pH 8.0, 1 mM EDTA, 1.5M NaCl). The DNA is ethanol precipitated and resuspended in H$_2$O at a concentration of 0.1 pmoles/$\|$ l.

Plasmid pJDB207/GAPFL-HIR (European Patent Application No. 225 633) contains the synthetic gene for desulphatohirudin (based on the E. coli codon usage) fused in frame to the signal sequence of yeast acid phosphatase (PH05). The gene is under the control of a short constitutive glyceraldehyd-3-phosphate dehydrogenase (GAPYL) promoter of yeast on shuttle vector pJDB207. 10 $\mu$g of plasmid pJDB207/GAPFL-HIR are digested with SalI and EcoRI. The 478 bp SalI-EcoRI fragment contains the Sal-Bam pBR322 part and the GAPFL promoter. The DNA fragment is isolated on a 0.8% preparative agarose gel, electroeluted and purified by DE52 chromatography and ethanol precipitation. The DNA is resuspended in H$_2$O at a concentration of 0.1 pmoles/$\mu$l. 5 $\mu$g of pJDB207/GAPFL-HIR are digested with SalI and BamHI. The large 6.7 kb vector fragment is isolated as described above.

0.2 pmoles of the 478 bp SalI-EcoRI promoter fragment, 0.2 pmoles of the 251 bp EcoRI-BamHI fragment containing the PH05 signal sequence and the synthetic hirullin P6 gene (HTI-P6 with preferred yeast codons) and 0.1 pmoles of the 6.7 kb vector fragment are ligated in 10 $\mu$l of 60 mM Tris-HCl pH 7.5, 10 mM MgCl$_2$, 5 mM DTT, 1 mM ATP and 200 units of T$^4$ DNA ligase (Biolabs) for 6 b at 15° C. A one $\mu$l aliquot of the ligation mixture is used to transform competent E. coli HB101 cells.

12 transformed, ampicillin resistant colonies are grown individually in LB medium containing 100 $\mu$g/ml of ampicillin. Plasmid DNA is prepared by the method of Holmes et al. (supra) and analysed by SalI/-HindIII double digests. A single clone with the expected restriction pattern is referred to as pJDB207/GAPFL-HTI-P6.

In an analogous construction the 248 bp EcoRI-BamHI fragment of the synthetic hirullin P18 gene (HTI-P18) is used. A single clone is referred to as pJDB207/GAPFL-HTI-P18.

In an analogous manner the construction can be performed with a 543 bp SalI-EcoRI promoter fragment of plasmid pJDB207/GAPEL-HIR (European Patent Application No. 225 633). The resulting new plasmids are referred to as pJDB207/GAPEL-HTI-P6 and pJDB207/GAPEL-HTI-P18.

Example 9

Construction of plasmid pJDB207/PH05(−173)-HTI-P6 pJDB207/PH05(-173)-HTI-P6 is a yeast plasmid for the expression of hirullin P6 under the control of a short PH05 promoter. The PH05(−173) promoter element comprises the nucleotide sequence of the yeast PH05 promoter from position −9 to −173 (BstEII restriction site), but has no upstream regulatory sequences (UAS). The PH05(−173) promoter therefore behaves like a constitutive promoter.

Plasmid pJDB207/PH05(Eco)-HIR (EP 225 633) contains the full length, regulated PH05 promoter with an EcoRI site introduced at position −8 with respect to the ATG of the PH05 signal sequence and the coding sequence of desulphatohirudin.

20 μg of plasmid pJDB207/PH05(Eco)-HIR are digested with BstEII. The sticky ends of the restriction fragments are filled in a reaction with Klenow DNA polymerase (I unit/pg DNA) in 200 μl of 60 mM Tris-HCl pH 7.5, 10 mM MgCl₂, 0.1 mM each of DATP, DCTP, DGTP, TTP for 30 min at room temperature. After phenol extraction the DNA is ethanol precipitated.

4.16 μg of BamHI linker (5'-CGGATCCG-3', Biolabs) are phosphorylated in 100 μl of 60 mm Tris-HCl pH 7.5, 10mM MgCl₂, 5 mM DTT, 0.5 mM ATP and 18 units of T4 polynucleotide kinase (Boehringer) for 45 min at 37° C. After 10 min at 75° C. the reaction mixture is slowly cooled to room temperature. The annealed oligonucleotide linkers are stored at −20° C.

4 pmoles of the [BstEII]/blunt end fragments of plasmid pJDB207/PH05(Eco)-HIR are incubated for 16 h at 15° C. with a 100fold excess of the phosphorylated and annealed BamHI linker in 208 μl of 60 mM Tris-HCl pH 7.5, 10 mM MgCl₂, 5 mM DTT, 3.5 mM ATP and 800 units of T4 DNA ligase (Biolabs). After inactivation of the ligase for 10 min at 85° C. the excess linkers are removed by precipitation of the DNA in the presence of 10 mm EDTA, 300 mM sodium acetate pH 6.0 and 0.54 volumes of isopropanol. The DNA is digested with BamHI and EcoRI. The DNA fragments are separated on a 0.8% preparative agarose gel. The 172 bp BamHI-EcoRI promoter fragment is recovered from the gel by electroelution and ethanol precipitation. The DNA is resuspended at a concentration of 0.1 pmoles/μl.

Plasmid pJDB207/GAPFL-HTI-P6 (see Example 8) is digested with EcoRI and HindIII. The 632 bp EcoRI-HindIII fragment is isolated as described above. The DNA fragment contains the PH05 signal sequence fused in frame to the coding sequence of hirullin P6 and the PH05 transcription termination fragment. Plasmid pJDB207/PH05(Eco)-HIR is cut with HindIII and BamHI. The 6.6 kb vector fragment is isolated.

0.2 pmoles each of the 172 bp BamHI-EcoRI fragment and the 632 bp EcoRI-HindIII fragment and 0.1 pmoles of the 6.6 kb vector fragment are ligated in 10 ml of 60 mM Tris-HCl pH 7.5, 10 mM MgCl₂, 5 mM DTT, 1 mM ATP and 400 units of T4 DNA ligase (Biolabs) for 6 h at 15° C. A one μl aliquot of the ligation mixture is added to 100 μl of calcium-treated, transformation-competent E. coli HB101 cells.

12 transformed, ampicillin resistant colonies are grown in LB medium containing 100 μg/ml of ampicillin. Plasmid DNA is prepared and analysed by BamHI and SalI/HindIII digests. One clone with the expected restriction fragments is selected and referred to as pJDB207/PH05(-173)-HTI-P6.

The 629 bp EcoRI-HindIII fragment of pJDB207/GAPFL-HTI-P18 (see Example 8) is used in an analogous construction, which results in plasmid pJDB207/PH05(-173)-HTI-P18.

Example 10

Construction of plasmid pDP34

Yeast 2 micron covalently closed circle DNA is isolated from Saccharomyces cerevisiae strain S288C. Cells are incubated with 5 μg/ml of Zymolyase (100,000 units/pg) for 20 min at 37° C. to digest the cell walls. The spheroplasts are lysed with 2% SDS. EDTA is then added to 25 mM, ethidium bromide to 1 mg/ml and caesium chloride to a final density of 1.55 g/ml. Plasmid DNA is separated from the chromosomal DNA by ultracentrifugation for 42 hours at 42,000 rpm at 15° C. The 2 micron plasmid DNA is cut from the gradient with a syringe. The ethidium bromide is removed by extraction with NaCl-saturated isopropanol and the plasmid DNA is finally ethanol precipitated. The purified two-micron plasmid DNA is then linearised with PstI and cloned into the PstI site of pUC19 [J. Norrander et al., Gene 26 (1983), 101] to give plasmid pDP31.

Plasmid pJDB207 is digested with the restriction enzymes KpnI and HpaI. The resulting 0.55 kb HpaI-KpnI fragment contains the junction between the 2 micron sequence and the defective promoter of the dLEU2 gene. Plasmid pUC7/LEU2 contains the yeast genomic 2.2 kb XhoI-SalI fragment of the LEU2 gene [A. Andreadis et al., Cell 31 (1982), 319] cloned into the SalI site of the plasmid pUC7 [J. Vieira et al., Gene 19 (1982), 259]. Plasmid pUC7/LEU2 is cut with KpnI and BpaI. The 4.25 kb KpnI-HpaI fragment is ligated to the 0.55 kb HpaI-KpnI fragment of pJDB207. This results in plasmid pDP30 where the original two micron/-dLEU2 fusion as in plasmid pJDB207 is placed in front of the LEU2 gene with its complete terminator. pDP30 is digested with HpaI and SalI and the 1.85 kb fragment containing the complete LEU2 gene is purified and cloned into the 8.7 kb SalI-HpaI fragment of plasmid pDP31. The resulting plasmid, pDP33 (see FIG. 3), is linearised by partial digestion with HindIII in the presence of 50 μg/ml ethidium bromide [M. Oesterlund et al., Gene 20 (1982) 121] and ligated with the 1.17 kb HindIII fragment containing the URAs gene [M. Rose et al., Gene 29 (1984), 113]. Insertion of the URAs gene is selected for by transformation into the E. coli strain pyrf (M. Rose et al., supra]. A positive clone is referred to as plasmid pDP34 (see FIG. 4).

pDP34 is a yeast-E. coli shuttle vector with the ampicillin resistance marker for E. coli and the URAs and dLEU2 yeast selective markers. It contains the complete 2 micron sequence in the A form and is REP1, REP2 and FLP proficient.

Example 11

Cloning of hirullin expression cassettes into PDP34

Plasmid pDP34 is digested with BamHI. The sticky ends of the restriction site are filled in a reaction with Klenow DNA polymerase (T. Maniatis et al., in: "Molecular Cloning. A Laboratory Manual", Cold Spring Harbor Laboratory, 1982). The DNA is further cut with SalI and the 11.8 kb vector fragment is isolated on a preparative 0.6% agarose gel. The DNA is recovered by electroelution and ethanol precipitation. Different expression cassettes are cloned into the pDP34 vector fragment between the SalI and [BamHI]/blunt end sites.

Figure 5:
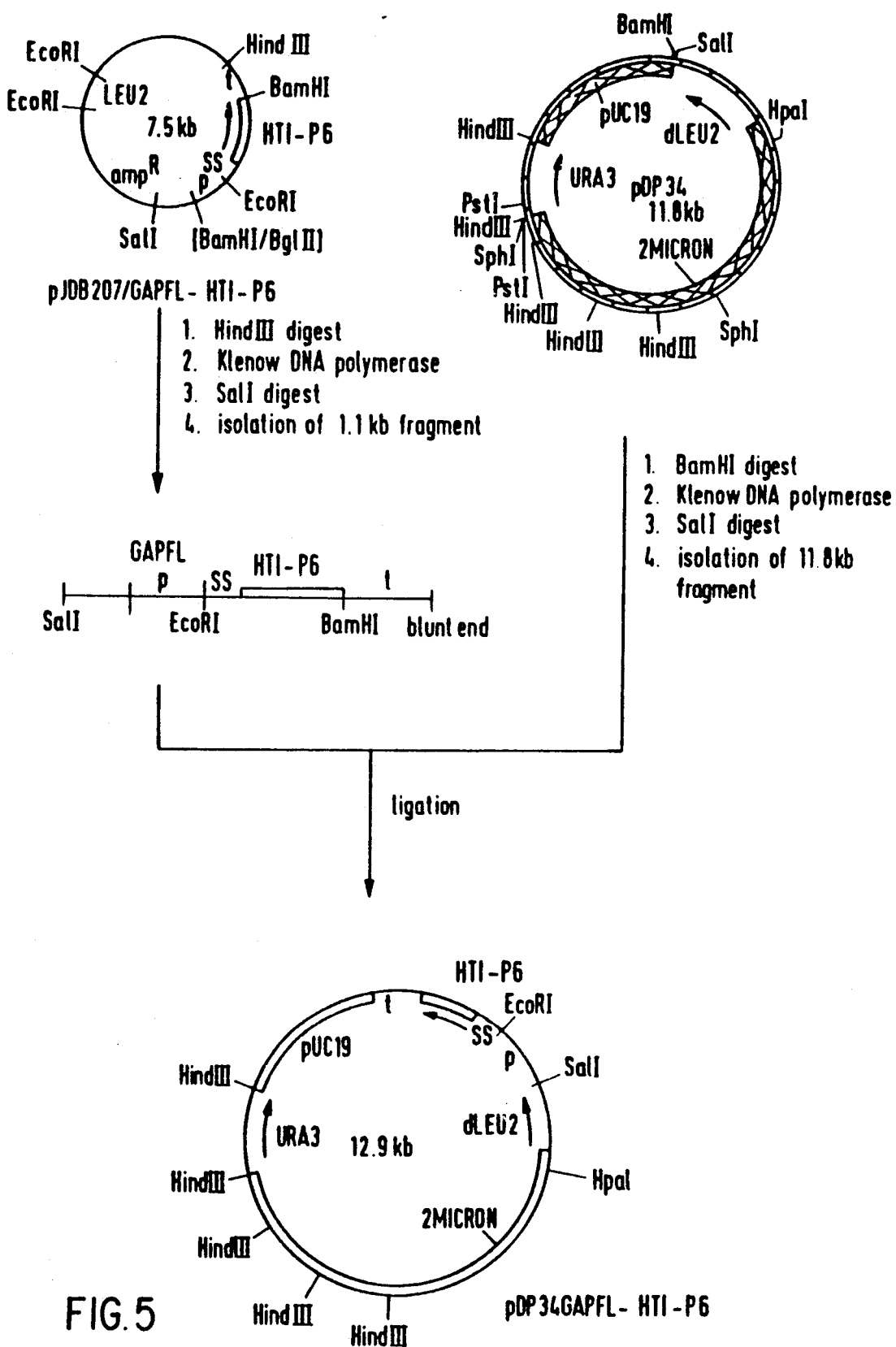
FIG. 5 schematically illustrates the construction of expression plasmid pDP34/GAPFL-HTI-P6.

Plasmid pJDB207/GAPFL-HTI-P6 (see Example 8) is digested with HindIII. The sticky ends are converted to blunt ends by Klenow DNA polymerase. The DNA is ethanol precipitated and further digested with SalI. The 1.1 kb SalI-(HindIIII/blunt end fragment contains the complete expression cassette with pBR322 sequences, the GAPFL promoter, the PH05 signal sequence fused in frame to the coding sequence (preferred yeast codons) of hirullin P6 and the PH05 transcription termination fragment. The 1.1 kb fragment is isolated on a preparative 0.8% agarose gel, recovered from the gel by electroelution and purified by DE52 ion exchange chromatography and ethanol precipitation. 0.2 pmoles of the 1.1 kb fragment and 0.1 pmoles of the 11.8 kb vector fragment are ligated in 10 µl of 60 mM Tris-HCl pH 7.5, 10 mM MgCl$_2$, 5 mM DTT, 3.5 mM ATP and 400 units of T4 DNA ligase (Biolabs) for 16 h at 15° C. A one µl aliquot is used to transform E. coli HB101 Ca$^{2+}$ cells. 5 transformed, ampicillin resistant colonies are analysed. Plasmid DNA is digested with BamHI and SalI/BamHI. One clone with the correct restriction fragments is selected and referred to as pDP34/GAPFL-HTI-P6 (see FIG. 5).

In an analogous manner the 1.1 kb SalI-[HindIIII/-blunt end fragments of pJDB207/GAPEL-HTI-P6, pJDB207/GAPFL-HTI-P18 and pJDB207/GAPEL-HTI-P18 (see Example 8) and plasmids pJDB207/PH05(-173)-HTI-P6 and pJDB207/PH05(-173)-HTI-P18 (see Example 9) are cloned into the pDP34 vector, which results in plasmids PDP34/GAPEL-HTI-P6, pDP34/GAPFL-HTI-P18, pDP34/GAPEL-HTI-P18, pDP34/PH05(-173)-HTI-P6 and pDP/PB05(-173)-HTI-PI8.

Example 12

The hirullin expression cassettes in plasmid pDP96 pDP96 has been constructed as an alternative to pDP34. The essential difference in the construction of pDP96 is the use of the unique SnaBI site in the two-micron circle for cloning as compared to the PstI site in pDP34. In pDP96 all known open reading frames of the two-micron circle, including the D reading frame, are intact. Therefore, the vector should be proficient for all known two-micron functions.

a) Construction of plasmid pDP96

Plasmid pDP31 (Example 10) is digested with PstI and SnaBI resulting in three fragments. Plasmid pK19 [conferring kanamycin resistance; Pridmore, R. D., Gene 56 (1987) 309-312] is linearized with SmaI. The DNA fragments of both digests are phenol extracted and precipitated with ethanol. The DNA fragments are mixed and ligated. The ligation mixture is transformed [Hanahan, D. J., Mol. Biol. 166 (1983) 557-580] into competent E. coli JM109 cell, [Yanisch-Perron, C. et al., Gene 33 (1985) 103-119], expressed for 2 h at 37° C. in LB medium and then plated on LB agar plates supplemented with 50 µg/ml of kanamycin, 30 µg/ml of XGal and 7 µg/ml of IPTG.

12 white, kanamycin-resistant colonies are grown. Plasmid DNA is analysed by XbaI and BamHI/KpnI digests. A single clone which bas lost the pUC19 vector part of pDP31, restored the two-micron D reading frame by religation of the PstI site and which has the pK19 plasmid blunt end inserted into the SnaBI site is referred to as pDP95. The plasmid contains the large SnaBI-PstI and the small PstI-SnaBI fragments of the two-micron plasmid cloned into the SmaI site of pK19. By religation of the PstI sites the D reading frame is reconstituted.

Plasmid pUC18/URA3 consists of the yeast 1.17 kb URAs gene (HindIII fragment) cloned at the HindIII site of the E. coli vector pUC18 with the URAs gene inserted in the opposite orientation as the ampicillin resistance gene. pUC18/URA3 is partially digested with the restriction enzyme HindIII in the presence of 50 µg/ml ethidium bromide for 1 h at 37° C. The addition of ethidium bromide to the digestion allows a first site to be digested by HindIII, but the subsequent intercalation of ethidium bromide into the linearised DNA interferes with the digestion of the second site, thus enriching for the linearised plasmid DNA. The restriction enzyme and ethidium bromide are removed by two consecutive phenol extractions and the DNA is ethanol precipitated. This DNA is then treated with the DNA polymerase large fragment (Klenow enzyme) to fill in the 5' overhangs of the HindIII sites. This end repaired DNA is run on an agarose gel to separate the various fragments, including the enriched, end repaired linear. The 3.35 kb pUC18/URA3 linear DNA is cut out of the gel and electro-eluted. This DNA is then self ligated with T4 DNA ligase, transformed into competent E. coli JM109 cells and plated onto YT plates supplemented with 50 µg/ml ampicillin. Colonies are screened as above to identify plasmid 'D', where the HindIII site at the pUC linker-array side of the URAs gene has been end repaired creating a new unique NheI restriction site. Plasmid 'D' is digested with the restriction enzyme HindIII to completion and the 5' overhangs are filled in a reaction with Klenow DNA polymerase. This DNA is then mixed with a large excess of NotI linkers (GCGGCCGC), ligated with T4 DNA ligase, transformed into competent E. coli JM109 cells and plated onto TY plates supplemented with 50 µg/ml ampicillin. Colonies are screened as above and plasmid 'E' is identified, where the HindIII site has been end repaired and a NotI linker added. Plasmid 'E' is digested with the restriction enzyme SacI, and the 3' overhangs are repaired with T4 DNA polymerase. The DNA is then mixed with a large excess of NotI linkers and ligated with T4 DNA ligase. This ligation mixture is transformed into competent E. coli JM109 cells and plated onto YT plates supplemented with 50 µg/ml ampicillin. Colonies are screened as above and plasmid pUC18/URA3-N is identified, where the pUC18 sequences are now flanked by NotI restriction sites (plasmids 'D' and 'E' are only intermediates in the construction of pUC18/URA3-N).

Plasmid pDP95 and pUC18/URA3-N are both digested with KpnI and BamHI resulting in two fragments each. The DNA fragments are mix-legated and used to transform competent E. coli JM109 cells. Cells are plated on to LB agar plates supplemented with 100 µg/ml of ampicillin, 30 µg/ml of XGal and 7 µg/ml of IPTG.

Figure 6:
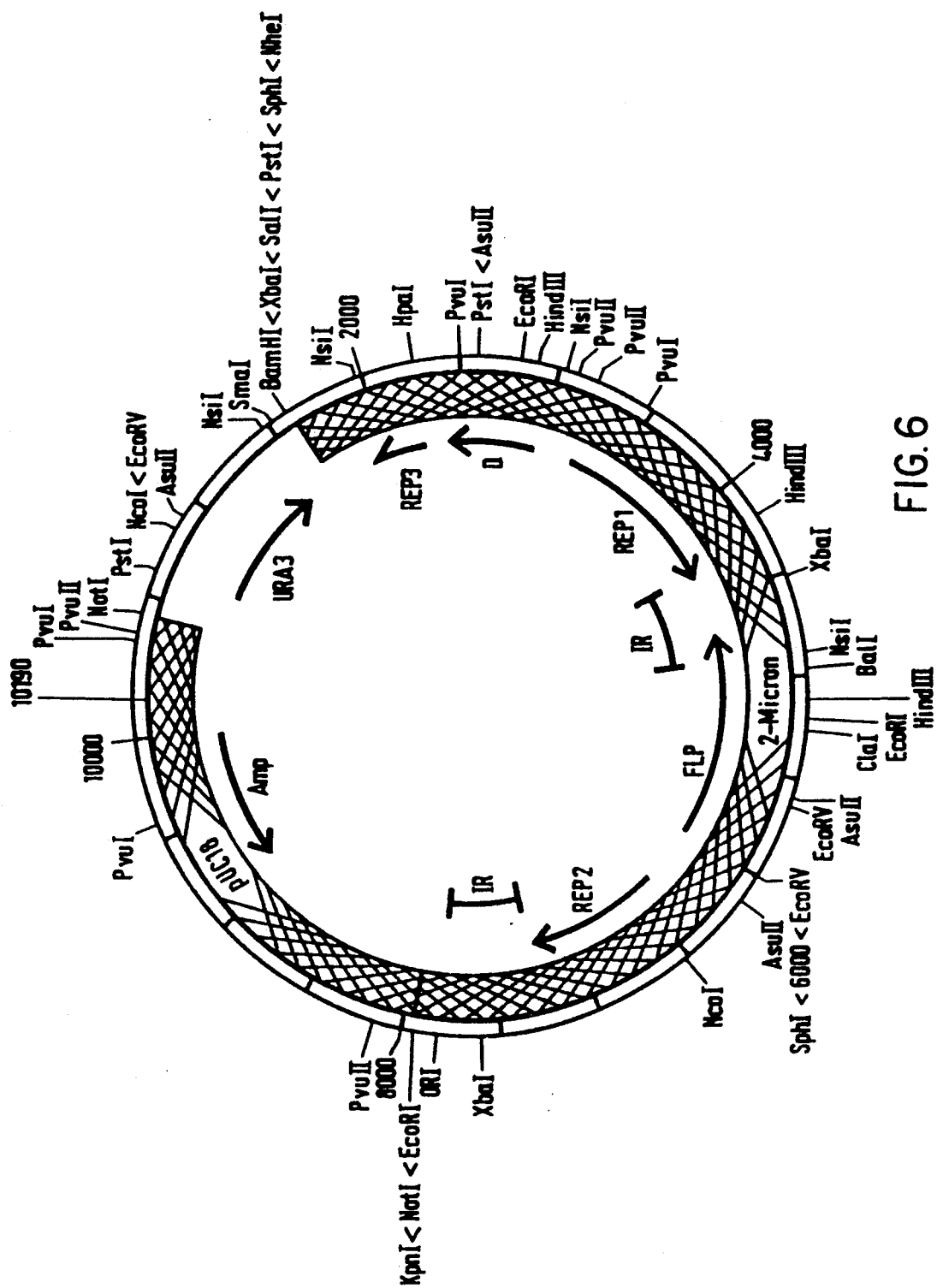
FIG. 6 is a schematic illustration of plasmid pDP96.

12 white, ampicillin-resistant colonies are grown. Plasmid DNA is analysed by HindIII and PvuII digests. A single clone is referred to as pDP96, comprising the complete two-micron sequence proficient for all its known functions and the URAs gene cloned into the pUC vector (see FIG. 6).

b) Cloning of hirullin expression cassettes into pDP96

In analogy to Example 11 pDP96 is digested with BamHI. The sticky ends are filled in a reaction with Klenow DNA polymerase. The DNA is further cut with SalI. The 10.2 kb vector fragment is isolated. The 1.1 kb SalI-[HindIIII/blunt end fragment of plasmid pJDB207/GAPFL-HTI-P6 (see Example 8) is isolated and ligated to the vector fragment.

6 transformed, ampicillin-resistant colonies are analysed. Plasmid DNA is digested with BamHI and SalI/BamHI. One clone with the expected restriction fragments is selected and referred to as pDP96/GAPFL-HTI-P6. In a similar way plasmid pDP96/GAPFL-HTI-P18 is obtained using the 1.1 kb SalI-[HindIII]/blunt end fragment of pJDB207/GAPFL-HTI-P18 (see Example 8).

Example 13

Construction of two-micron DNA free *Saccharomyces cerevisiae* host strains

In order to remove the endogenous two-micron plasmid, in a first step a deletion is introduced in the URA3 gene of strain HT246 (DSM 4084; α leu 2-3, leu 2-112, prb) to make the strain auxotrophic for uracil. HT246 is transformed with 1 μg of plasmid YFp13 [Broach, J. R., Strathern, J. N., Hicks, J. B. (1979) Gene 8, 121–123] using the transformation protocol described by Hinnen et al. [Proc. Natl. Acad. Sci. USA 75, 1929 (1978)]. 10 μg of plasmid pUC12ura3Δ containing a deletion in the URA3 gene [Sengstag, Cb., Hinnen, A., Nucleic Acids Research 15, 233–246 (1987)] are added along with plasmid YEp13. Roughly 3000 leucine prototrophic transformants are resuspended in 5 ml minimal medium (Difco Yeast Nitrogen Base without amino acids to which 2% glucose, 0.1% leucine, 0.1% uracil and 0.25% fluoroorotic acid are added) in a small shake flask and incubated for 60 hours at 30° C. and 180 r.p.m. Transformants which grow are resistant to the toxic analogue fluoroorotic acid and carry therefore a replacement in the chromosomal URA3 gene by ura3Δ. The grown cells are plated out on full medium composed of (g/l): Peptone 20, yeast extract 10, glucose 20, and after growth for 48 h at 30° C. replica-plated onto minimal medium (Difco yeast nitrogen base without amino acids, supplemented with 2% glucose and 0.1% leucine) to detect uracil auxotrophs. Several auxotrophs are picked and tested for plasmid YEp13 loss conferring leucine auxotrophy. One individual colony (designated Tr889) requiring leucine and uracil is picked and used for further experimentation.

Figure 4:
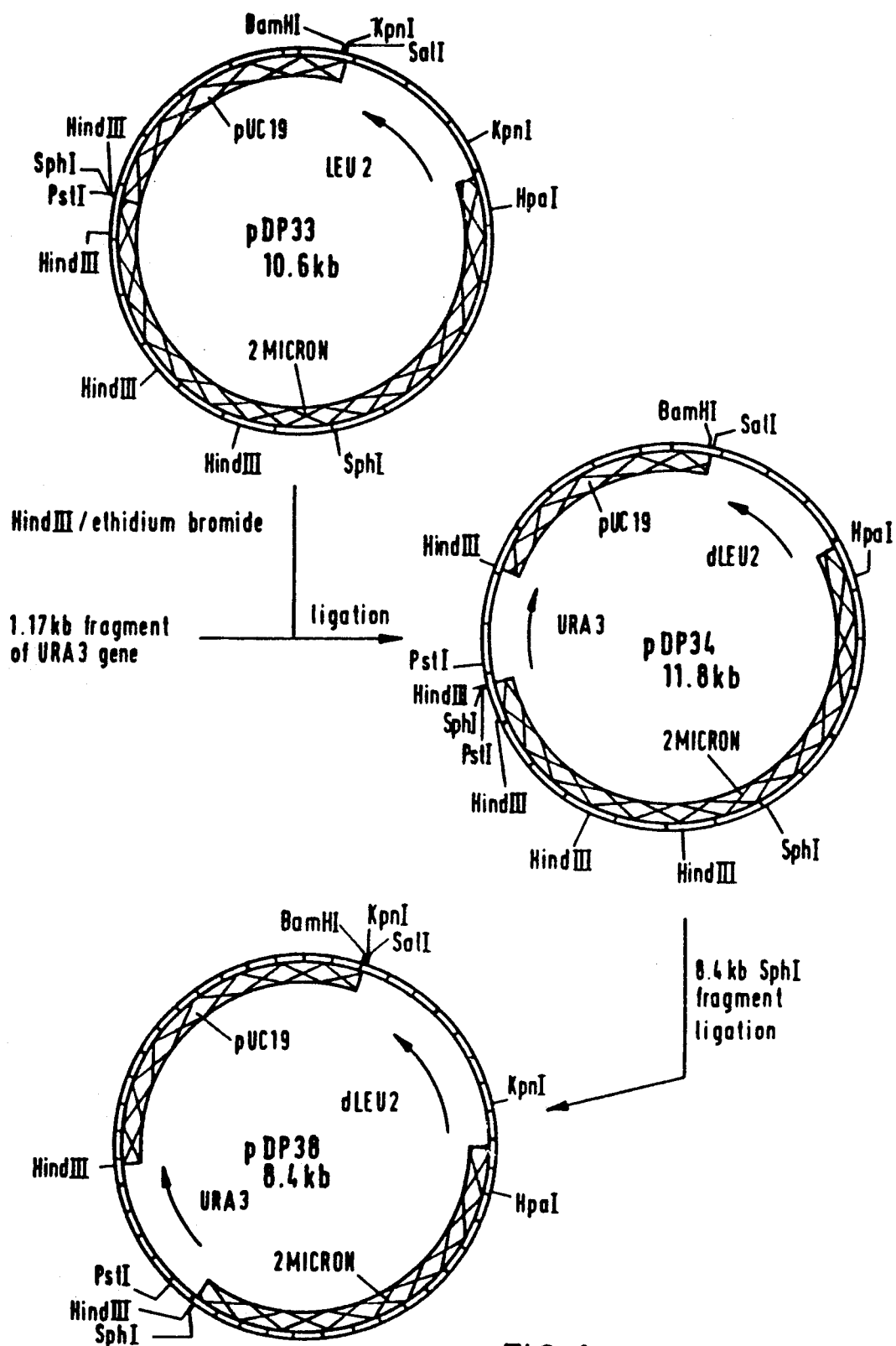
FIG. 4 schematically illustrates the construction of plasmids pDP31 and pDP38.

Tr889 is transformed with plasmid pDP38 [obtained from plasmid pDP34 by digestion with SphI and religation of the resulting 8.4 kb fragment; see FIG. 4], which carries both marker genes LEU2 and URA3 (transformation protocol, supra). Transformed yeast cells are first selected on yeast minimal media plates deficient in uracil, supplemented with leucine and then replica-plated onto minimal medium deficient in leucine and supplemented with uracil. 10 weakly growing colonies are picked and individually grown in liquid full medium (supra) over about a hundred generations. By doing so, the cells lose the pDP38 plasmid and—to a certain percentage—simultaneously also the endogenous two-micron plasmid. 10 uracil and leucine requiring colonies are picked, DNA is prepared, the DNA is digested to completion with PstI and probed with $^{32}$P-labelled yeast two-micron DNA on Southern blots. One isolate without any hybridisation signal is referred to as H449 (a, leu2-3, leu2-112, ura3Δ, prb, cir°), an isogenic two-micron free (cir°) derivative of yeast strain HT246.

Example 14

Transformation of *S. cerevisiae* strain H449

*Saccharomyces cerevisiae* strain H449 is transformed with plasmids
pDP34/GAPFL-HTI-P6
pDP34/GAPFL-HTI-P18
pDP34/GAPEL-HTI-P6
pDP34/GAPEL-HTI-P18
pDP34/PH05(−173)-HTI-P6
pDP34/PH05(−173)-HTI-P18
pDP96/GAPFL-HTI-P6
pDP96/GAPFL-HTI-P18
using the transformation protocol described by Hinnen et al. [Proc. Natl. Acad. Sci. USA 75, 1929 (1978)]. Transformed yeast cells are selected on yeast minimal medium plates supplemented with leucine and deficient in uracil. Single transformed yeast cells are isolated and referred to as
*Saccharomyces cerevisiae* H449/pDP34/GAPFL-HTI-P6
*Saccharomyces cerevisiae* H449/pDP34/GAPFL-HTI-P18
*Saccharomyces cerevisiae* H449/pDP34/GAPEL-HTI-P6
*Saccharomyces cerevisiae* H449/pDP34/GAPEL-HTI-P18
*Saccharomyces cerevisiae* H449/pDP34/PHO5(-173)-HTI-P6
*Saccharomyces cerevisiae* H449/pDP34/PHO5(-173)-HTI-P18
*Saccharomyces cerevisiae* H449/pDP96/GAPFL-HTI-P6
*Saccharomyces cerevisiae* H449/pDP96/GAPFL-HTI-P18

Example 15

Fermentation of transformed yeast strains on a laboratory scale

Cells of *Saccharomyces cerevisiae* H449/pDP34/GAPFL-HTI-P6 and of *Saccharomyces cerevisiae* H449/pDP34/GAPFL-HTI-P18 are each grown in two subsequent precultures of 10 ml minimal medium composed of (g/l):

| Difco Yeast Nitrogen Base | 6.7 |
|---|---|
| asparagine | 10 |
| leucine | 1 |
| glucose | 20 |

The first preculture is grown for 60 h at 28° C. and 180 r.p.m. The second preculture is inoculated with 2% of the first preculture and incubated for 24 h at 28° C. and 180 r.p.m.

The main culture medium is composed of (g/l):

| yeast extract | 49 |
|---|---|
| glucose | 5 |
| fructose | 57 |
| NH$_4$NO$_3$ | 0.5 |
| MgSO$_4$ × 7H$_2$O | 1.0 |
| CaCO$_3$ | 5.0 |
| Ca$_3$(PO$_4$)$_2$ | 2.0 |

The main culture is inoculated with about $2 \times 10^6$ cells/ml and incubated up to 72 h at 28° C. and 180 r.p.m. Approximately $1 \times 10^9$ cells/ml are obtained at the end of the fermentation. At several time points during the fermentation aliquots of the cultures are taken, the cells removed by centrifugation and the culture supernatant analysed for hirullin by HPLC (infra).

Example 16

Recovery of hirullins from culture broths of transformed *S. cerevisiae*

The culture broth is mixed with Amberlite XAD-7 and is subjected to adsorption for about 4 hours at 25° C. The cells are separated from the resin in a column.

After washing with 1M NaCl the resin is eluted with Tris buffer (50 mM, pH 7.0–8.5). The main fraction is adjusted to pH 2.9 and is applied onto a Sephadex G50 superfine column (Pharmacia 100 cm×26 mm; 400 ml bed volume) preequilibrated with 0.1M acetic acid and connected to a Pharmacia FPLC system. The elution is carried out with 0.1M acetic acid at a flow rate of 0.2 ml/min and monitored at 280 nm.

6 ml fractions are collected and tested for activity with a thrombin inhibition assay as described by S. Mao et al. [Anal. Bioch. 161, 514 (1987)]. This step gives a 4-fold purification. The active fractions are dried on a lyophilizer, redissolved in 2 ml 0.02M histidine/HCl pH 5.6 (=eluent A), centrifuged and the clear supernatant applied onto a Q Sepharose fast flow anion exchanger column (Pharmacia, 40 cm×16 mm; bed volume 66 ml) connected to a pharmacia FPLC system and preequilibrated with eluent A. Elution is done with a step gradient at a flow rate of 2 ml/min: 48 min 0% B (eluent B: 0.02M histidine/HCl pH 5.6+1M NaCl), 102 min 15% B, 65 min 100% B. The run is monitored at 280 nm and the active fractions are pooled and desalted on a Sephadex G50 fine column with 0.01M NH$_4$HCO$_3$, then freeze-dried.

The final purification is done by reversed phase HPLC (Nucleosil C18 and phenyl silica) and by Mono Q anion exchange chromatography as described in Example 3. The pure hirullins P6 and P18 produced by *S. cerevisiae* correspond essentially to the products obtained according to the procedure described in Example 6, i.e. the resulting hirullin P6 is devoid of the sulphate monoester group at Tyr$^{61}$ (=desulphatohirullin P6).

Example 17

Pharmaceutical composition containing a hirullin compound for parenteral administration A solution containing a hirullin compound according to any one of Examples 3, 5 or 16 is dialysed against a 0.9% NaCl solution. The concentration of the solution is then adjusted by diluting with the same NaCl solution to 0.2 mg/ml or 2 mg/ml. These solutions are sterilized by ultrafiltration (membranes with 0.22 μm pores).

The sterilized solutions can be used directly, for example for intravenous administration.

Deposition of microorganisms

The following microorganism strains were deposited at the Deutsche Sammlung von Mikroorganismen (DSM), Mascheroder Weg 1b, D-3300 Braunschweig (deposition dates and accession numbers given):

*Saccharomyces cerevisiae* H449: Feb. 18, 1988, DSM 4413;

*Escherichia coli* JM109/pDP38: Feb. 19, 1988, DSM 4414;

*Escherichia coli* JM109/pDP34: Mar. 14, 1988, DSM 4473.

We claim:

1. An isolated and purified DNA sequence encoding a hirullin polypeptide of the formula

MRYTACTESG QNQCICEGND     (FORMULA I)

VCGQGRNCQF DSSGKKCVEG EGT*RKPQNEG $$\overset{Z}{\underset{|}{\text{QHDFDPIPEE YLS}}}$$

or

VSYTDCTSGQ NYCLCGGNFC     (FORMULA II)

GDGKHCEMDG SENKCVDGEG TPKRQT*SGPS

DFEEFSLDDI EQ wherein T* represents threonine, hydroxy group of which is free, and Z represents the phenolic hydrogen atom of tyrosine.

2. A hybrid vector, comprising an expression control sequence operably linked in proper reading frame to a DNA sequence of claim 1.

3. A microorganism transformed with a hybrid vector of claim 2.

* * * * *